(12) United States Patent
Hansen et al.

(10) Patent No.: US 12,161,581 B2
(45) Date of Patent: Dec. 10, 2024

(54) METHOD OF MONITORING PERFORMANCE OF AN OSTOMY DEVICE WITH A MONITOR DEVICE ATTACHABLE TO BOTH AN OSTOMY APPLIANCE AND AN ACCESSORY DEVICE

(71) Applicant: Coloplast A/S, Humlebaek (DK)

(72) Inventors: Jais Ask Hansen, Jaegerspris (DK); Niels Hvid, Vedbaek (DK); Finn Speiermann, Virum (DK); Lars Erup Larsen, Maaloev (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 18/541,136

(22) Filed: Dec. 15, 2023

(65) Prior Publication Data

US 2024/0180740 A1    Jun. 6, 2024

Related U.S. Application Data

(63) Continuation of application No. 17/975,626, filed on Oct. 28, 2022, now Pat. No. 11,974,938, which is a continuation of application No. 16/954,527, filed as application No. PCT/DK2018/050400 on Dec. 20, 2018, now Pat. No. 11,865,029.

(30) Foreign Application Priority Data

Dec. 22, 2017   (DK) .......................... PA 2017 71001

(51) Int. Cl.
| | | |
|---|---|---|
| *A61F 5/443* | (2006.01) | |
| *A61B 5/00* | (2006.01) | |
| *A61F 5/44* | (2006.01) | |
| *A61F 5/445* | (2006.01) | |

(52) U.S. Cl.
CPC ............ *A61F 5/443* (2013.01); *A61B 5/0002* (2013.01); *A61B 5/4851* (2013.01); *A61F 5/4404* (2013.01); *A61F 5/445* (2013.01); *A61B 2560/0204* (2013.01); *A61B 2560/0271* (2013.01); *A61B 2560/0456* (2013.01)

(58) Field of Classification Search
CPC ........ A61F 5/443; A61F 5/4404; A61F 5/445; A61B 5/0002
See application file for complete search history.

(56) References Cited

U.S. PATENT DOCUMENTS

| | | |
|---|---|---|
| 2,054,535 A | 9/1936 | Diack |
| 2,327,514 A | 8/1943 | Fenwick |
| 2,542,233 A | 2/1951 | Carroll |
| 2,544,579 A | 3/1951 | Ardner |
| 3,214,502 A | 10/1965 | Schaar |
| 3,808,354 A | 4/1974 | Feezor et al. |

(Continued)

FOREIGN PATENT DOCUMENTS

| | | |
|---|---|---|
| AU | 2007342523 B2 | 7/2011 |
| CA | 2540756 C | 1/2008 |

(Continued)

*Primary Examiner* — Guy K Townsend
(74) *Attorney, Agent, or Firm* — Coloplast Corp., Coloplast A/S; Nick Baumann

(57) ABSTRACT

A method of monitoring performance of an ostomy device includes monitoring moisture information with a monitor device attachable to a sensor and transferring the moisture information from the monitor device to an accessory device.

15 Claims, 15 Drawing Sheets

(56) References Cited

U.S. PATENT DOCUMENTS

| | | |
|---|---|---|
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A * | 5/1991 | Williams ............ A61N 1/0587 607/129 |
| 5,051,259 A | 9/1991 | Olsen et al. |
| 5,074,851 A | 12/1991 | Plass et al. |
| 5,111,812 A | 5/1992 | Swanson et al. |
| 5,167,650 A | 12/1992 | Johnsen et al. |
| 5,197,895 A | 3/1993 | Stupecky |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,519,644 A | 5/1996 | Benton |
| 5,570,082 A | 10/1996 | Mahgerefteh et al. |
| 5,593,397 A | 1/1997 | La Gro |
| 5,672,163 A | 9/1997 | Ferreira et al. |
| 5,677,221 A | 10/1997 | Tseng |
| 5,704,905 A | 1/1998 | Jensen et al. |
| 5,714,225 A | 2/1998 | Hansen et al. |
| 5,790,036 A | 8/1998 | Fisher et al. |
| 5,800,415 A | 9/1998 | Olsen |
| 5,816,252 A | 10/1998 | Faries, Jr. et al. |
| 5,834,009 A | 11/1998 | Sawers et al. |
| 5,846,558 A | 12/1998 | Nielsen et al. |
| 5,876,855 A | 3/1999 | Wong et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,057,689 A | 5/2000 | Saadat |
| 6,078,261 A | 6/2000 | Davsko |
| 6,103,033 A | 8/2000 | Say et al. |
| 6,135,986 A | 10/2000 | Leisner et al. |
| 6,165,005 A | 12/2000 | Mills et al. |
| 6,171,289 B1 | 1/2001 | Millot et al. |
| 6,206,864 B1 | 3/2001 | Kavanagh et al. |
| 6,241,704 B1 | 6/2001 | Peterson et al. |
| 6,246,330 B1 | 6/2001 | Nielsen |
| 6,270,445 B1 | 8/2001 | Dean, Jr. et al. |
| 6,297,422 B1 | 10/2001 | Hansen et al. |
| 6,407,308 B1 | 6/2002 | Roe et al. |
| 6,433,244 B1 | 8/2002 | Roe et al. |
| 6,433,695 B1 | 8/2002 | Kai et al. |
| 6,482,491 B1 | 11/2002 | Samuelsen et al. |
| 6,485,476 B1 | 11/2002 | von Dyck et al. |
| 6,520,943 B1 | 2/2003 | Wagner |
| 6,659,989 B1 | 12/2003 | Otto |
| 6,764,474 B2 | 7/2004 | Nielsen et al. |
| 7,049,478 B1 | 5/2006 | Smith |
| 7,066,919 B1 * | 6/2006 | Sauerland ................ A61F 5/44 604/327 |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,221,279 B2 | 5/2007 | Nielsen |
| 7,326,190 B2 | 2/2008 | Botten |
| 7,341,578 B2 | 3/2008 | Bulow et al. |
| 7,347,844 B2 | 3/2008 | Cline et al. |
| 7,367,965 B2 | 5/2008 | Poulsen et al. |
| 7,422,578 B2 | 9/2008 | Shan et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 * | 3/2010 | McCall ............ A61M 1/3655 210/651 |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,326,051 B1 | 12/2012 | Hobbs |
| 8,398,575 B1 | 3/2013 | McCall |
| 8,398,603 B2 * | 3/2013 | Thirstrup ............ A61B 5/746 602/41 |
| 8,399,732 B2 | 3/2013 | Oelund et al. |
| 8,409,158 B2 * | 4/2013 | Edvardsen ............ A61F 5/443 604/335 |
| 8,439,883 B1 | 5/2013 | Johnsen |
| 8,449,471 B2 | 5/2013 | Tran |
| 8,474,338 B2 | 7/2013 | Gelman et al. |
| 8,500,718 B2 | 8/2013 | Locke et al. |
| 8,507,081 B2 | 8/2013 | Strobech et al. |
| 8,632,492 B2 | 1/2014 | DeLegge |
| 8,680,991 B2 | 3/2014 | Tran |
| 8,684,982 B2 | 4/2014 | Nguyen-DeMary et al. |
| 8,740,865 B2 | 6/2014 | Krystek et al. |
| 8,795,257 B2 | 8/2014 | Coulthard et al. |
| D712,545 S | 9/2014 | Igwebuike et al. |
| 8,821,464 B2 * | 9/2014 | Hanuka ............ A61F 5/441 604/333 |
| 8,975,465 B2 | 3/2015 | Hong et al. |
| 8,979,813 B2 | 3/2015 | Uveborn |
| 9,046,085 B2 | 6/2015 | Schoess et al. |
| 9,066,812 B2 * | 6/2015 | Edvardsen ............ A61F 5/443 |
| 9,216,104 B2 | 12/2015 | Thirstrup et al. |
| 9,308,332 B2 * | 4/2016 | Heppe .................... A61M 1/30 |
| 9,322,797 B1 * | 4/2016 | Lastinger ............ G01N 27/12 |
| 9,566,383 B2 | 2/2017 | Yodfat et al. |
| 9,629,779 B2 | 4/2017 | Grum-Schwensen et al. |
| 9,629,964 B2 * | 4/2017 | Wuepper ................ G01M 3/16 |
| 9,675,267 B2 | 6/2017 | Laakkonen et al. |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 * | 1/2018 | Heppe ................ A61M 1/3656 |
| 9,928,341 B2 * | 3/2018 | Angelides ............ G16H 40/67 |
| 10,016,298 B2 * | 7/2018 | Thirstrup ................ A61F 13/42 |
| D826,740 S | 8/2018 | Stevens et al. |
| 10,426,342 B2 | 10/2019 | Hresko et al. |
| 10,500,084 B2 * | 12/2019 | Hansen .................... A61F 5/443 |
| 10,531,977 B2 * | 1/2020 | Schoess .................... A61F 5/445 |
| 10,646,370 B2 | 5/2020 | Keleny et al. |
| 10,792,184 B2 * | 10/2020 | Hvid .................... A61M 3/0216 |
| 10,799,385 B2 * | 10/2020 | Hansen .................... G01M 3/40 |
| 10,849,781 B2 | 12/2020 | Hansen et al. |
| 10,874,541 B2 | 12/2020 | Seres et al. |
| 10,987,243 B2 * | 4/2021 | Thirstrup ............ A61B 5/746 |
| 11,096,818 B2 * | 8/2021 | Thirstrup ............ A61F 13/02 |
| 11,135,084 B2 | 10/2021 | Seres et al. |
| 11,219,436 B2 | 1/2022 | Mayberg |
| 11,238,133 B2 | 2/2022 | Brewer et al. |
| 11,306,224 B2 | 4/2022 | Chatterjee et al. |
| 11,406,525 B2 * | 8/2022 | Seres ....................... A61F 5/445 |
| 11,471,318 B2 * | 10/2022 | Hansen .................... A61F 5/448 |
| 11,491,042 B2 | 11/2022 | Seres et al. |
| 11,534,323 B2 * | 12/2022 | Hansen .................... A61F 2/64 |
| 11,540,937 B2 * | 1/2023 | Hansen ............ A61B 5/4283 |
| 11,547,595 B2 | 1/2023 | Hansen et al. |
| 11,547,596 B2 * | 1/2023 | Hansen .................... A61F 5/44 |
| 11,559,423 B2 * | 1/2023 | Speiermann ........ A61F 5/445 |
| 11,559,426 B2 * | 1/2023 | Sletten ................ A61F 5/445 |
| 11,589,811 B2 * | 2/2023 | Hansen ............ A61B 5/7455 |
| 11,590,015 B2 * | 2/2023 | Hansen .................... A61F 5/443 |
| 11,607,334 B2 * | 3/2023 | Hansen .................... A61F 5/44 |
| 11,612,512 B2 | 3/2023 | Hansen et al. |
| 11,622,719 B2 * | 4/2023 | Hansen .................... A61F 5/443 600/301 |
| 11,627,891 B2 * | 4/2023 | Hansen .................... G06T 7/74 382/128 |
| 11,628,084 B2 * | 4/2023 | Hansen ............ A61B 5/6833 604/344 |

(56) References Cited

U.S. PATENT DOCUMENTS

| | | | |
|---|---|---|---|
| 11,654,043 B2* | 5/2023 | Hansen | A61F 5/445 604/344 |
| 2001/0041920 A1 | 11/2001 | Starkweather et al. | |
| 2001/0051787 A1 | 12/2001 | Haller et al. | |
| 2002/0013613 A1 | 1/2002 | Haller et al. | |
| 2002/0019615 A1 | 2/2002 | Roe et al. | |
| 2002/0109621 A1 | 8/2002 | Khair et al. | |
| 2003/0132763 A1 | 7/2003 | Ellenz | |
| 2003/0169032 A1 | 9/2003 | Minchole et al. | |
| 2004/0006320 A1 | 1/2004 | Buglino et al. | |
| 2004/0030305 A1 | 2/2004 | Sakamoto | |
| 2004/0036484 A1 | 2/2004 | Tamai | |
| 2004/0049145 A1 | 3/2004 | Flick | |
| 2004/0068244 A1 | 4/2004 | Salone et al. | |
| 2004/0078219 A1* | 4/2004 | Kaylor | G16H 40/67 600/300 |
| 2004/0100376 A1* | 5/2004 | Lye | A61B 5/411 600/300 |
| 2004/0106908 A1 | 6/2004 | Leise, Jr. et al. | |
| 2004/0111072 A1 | 6/2004 | McKissick | |
| 2004/0133175 A1 | 7/2004 | Hagedorn-Olsen | |
| 2004/0171999 A1 | 9/2004 | Andersen et al. | |
| 2004/0193122 A1 | 9/2004 | Cline et al. | |
| 2004/0193123 A1 | 9/2004 | Fenton | |
| 2004/0216833 A1 | 11/2004 | Fleming et al. | |
| 2005/0038325 A1 | 2/2005 | Moll | |
| 2005/0054997 A1 | 3/2005 | Buglino et al. | |
| 2005/0065488 A1 | 3/2005 | Elliott | |
| 2005/0070863 A1 | 3/2005 | von Bulow et al. | |
| 2005/0085779 A1 | 4/2005 | Poulsen et al. | |
| 2005/0101841 A9* | 5/2005 | Kaylor | G16H 40/67 600/300 |
| 2005/0240163 A1 | 10/2005 | Andersen | |
| 2005/0256545 A1 | 11/2005 | Koh et al. | |
| 2005/0261645 A1 | 11/2005 | Conrad et al. | |
| 2006/0015081 A1 | 1/2006 | Suzuki et al. | |
| 2006/0025727 A1 | 2/2006 | Boehringer et al. | |
| 2006/0052752 A1 | 3/2006 | McMichael | |
| 2006/0194324 A1* | 8/2006 | Faries, Jr. | A61B 46/10 436/1 |
| 2006/0271002 A1 | 11/2006 | Botten | |
| 2007/0010256 A1 | 1/2007 | Klabunde et al. | |
| 2007/0035405 A1 | 2/2007 | Wada et al. | |
| 2007/0135782 A1 | 6/2007 | Bager et al. | |
| 2007/0185464 A1 | 8/2007 | Fattman et al. | |
| 2007/0203407 A1 | 8/2007 | Hoss et al. | |
| 2007/0204691 A1 | 9/2007 | Bogner et al. | |
| 2008/0038536 A1 | 2/2008 | Strobech et al. | |
| 2008/0041792 A1 | 2/2008 | Crnkovich et al. | |
| 2008/0071214 A1 | 3/2008 | Locke et al. | |
| 2008/0075934 A1 | 3/2008 | Barlow, Jr. et al. | |
| 2008/0091154 A1 | 4/2008 | Botten | |
| 2008/0096726 A1 | 4/2008 | Riley et al. | |
| 2008/0097360 A1 | 4/2008 | Andersen et al. | |
| 2008/0140057 A1 | 6/2008 | Wood et al. | |
| 2008/0234641 A1 | 9/2008 | Locke et al. | |
| 2008/0255808 A1 | 10/2008 | Hayter | |
| 2008/0275327 A1* | 11/2008 | Faarbaek | A61B 5/6833 600/382 |
| 2008/0278337 A1 | 11/2008 | Huang et al. | |
| 2008/0300559 A1 | 12/2008 | Gustafson et al. | |
| 2008/0300578 A1 | 12/2008 | Freedman | |
| 2008/0306459 A1 | 12/2008 | Albrectsen | |
| 2009/0012501 A1 | 1/2009 | Boehringer et al. | |
| 2009/0118600 A1 | 5/2009 | Ortiz et al. | |
| 2009/0118687 A1 | 5/2009 | Kristensen et al. | |
| 2009/0167286 A1 | 7/2009 | Naylor et al. | |
| 2009/0173935 A1 | 7/2009 | Cho et al. | |
| 2009/0216169 A1 | 8/2009 | Hansen et al. | |
| 2009/0227969 A1 | 9/2009 | Jaeb et al. | |
| 2009/0234916 A1 | 9/2009 | Cosentino et al. | |
| 2009/0247970 A1 | 10/2009 | Keleny et al. | |
| 2009/0264957 A1 | 10/2009 | Giftakis et al. | |
| 2010/0010460 A1 | 1/2010 | Butler | |
| 2010/0030167 A1* | 2/2010 | Thirstrup | A61F 5/4404 340/657 |
| 2010/0036206 A1 | 2/2010 | Lorio | |
| 2010/0072271 A1 | 3/2010 | Thorstensson | |
| 2010/0076275 A1 | 3/2010 | Chu et al. | |
| 2010/0106220 A1 | 4/2010 | Ecker et al. | |
| 2010/0114047 A1 | 5/2010 | Song et al. | |
| 2010/0271212 A1 | 10/2010 | Page | |
| 2010/0311167 A1 | 12/2010 | Wood et al. | |
| 2011/0034890 A1 | 2/2011 | Stroebech et al. | |
| 2011/0077497 A1 | 3/2011 | Oster et al. | |
| 2011/0130642 A1 | 6/2011 | Jaeb et al. | |
| 2011/0144470 A1 | 6/2011 | Mazar et al. | |
| 2011/0191044 A1 | 8/2011 | Stafford | |
| 2011/0245682 A1 | 10/2011 | Robinson et al. | |
| 2011/0246983 A1 | 10/2011 | Brunet et al. | |
| 2011/0257496 A1 | 10/2011 | Terashima et al. | |
| 2012/0013130 A1 | 1/2012 | Jung | |
| 2012/0089037 A1 | 4/2012 | Bishay et al. | |
| 2012/0143154 A1* | 6/2012 | Edvardsen | A61F 5/4404 604/336 |
| 2012/0143155 A1* | 6/2012 | Edvardsen | A61F 5/443 604/318 |
| 2012/0253224 A1 | 10/2012 | Mir et al. | |
| 2012/0258302 A1 | 10/2012 | Hunt et al. | |
| 2012/0259230 A1 | 10/2012 | Riley | |
| 2012/0283678 A1 | 11/2012 | Nguyen-DeMary et al. | |
| 2012/0304767 A1 | 12/2012 | Howard et al. | |
| 2012/0323086 A1 | 12/2012 | Hansen | |
| 2013/0018231 A1 | 1/2013 | Hong et al. | |
| 2013/0030167 A1 | 1/2013 | Wang et al. | |
| 2013/0030397 A1 | 1/2013 | Sabeti | |
| 2013/0060213 A1* | 3/2013 | Hanuka | A61F 5/441 604/344 |
| 2013/0066285 A1 | 3/2013 | Locke et al. | |
| 2013/0072886 A1 | 3/2013 | Schertiger et al. | |
| 2013/0078912 A1 | 3/2013 | San Vicente et al. | |
| 2013/0086217 A1 | 4/2013 | Price et al. | |
| 2013/0102979 A1 | 4/2013 | Coulthard et al. | |
| 2013/0138065 A1 | 5/2013 | Buus | |
| 2013/0150769 A1 | 6/2013 | Heppe | |
| 2013/0165862 A1 | 6/2013 | Griffith et al. | |
| 2013/0192604 A1 | 8/2013 | Persson et al. | |
| 2013/0226116 A1 | 8/2013 | Edvardsen et al. | |
| 2013/0231620 A1 | 9/2013 | Thirstrup | |
| 2013/0261575 A1 | 10/2013 | Kiyoshi | |
| 2013/0267790 A1 | 10/2013 | Pfuetzner et al. | |
| 2013/0303867 A1 | 11/2013 | Elfstrom et al. | |
| 2013/0324952 A1 | 12/2013 | Krystek et al. | |
| 2013/0324955 A1 | 12/2013 | Wong et al. | |
| 2013/0332085 A1 | 12/2013 | Yang et al. | |
| 2014/0051946 A1 | 2/2014 | Arne et al. | |
| 2014/0128815 A1 | 5/2014 | Cabiri et al. | |
| 2014/0200426 A1 | 7/2014 | Taub et al. | |
| 2014/0200538 A1 | 7/2014 | Euliano et al. | |
| 2014/0236111 A1 | 8/2014 | Casado et al. | |
| 2014/0236335 A1 | 8/2014 | Lewis et al. | |
| 2014/0275854 A1 | 9/2014 | Venkatraman et al. | |
| 2014/0276501 A1 | 9/2014 | Cisko | |
| 2014/0288381 A1 | 9/2014 | Faarbaek et al. | |
| 2014/0303574 A1 | 10/2014 | Knutson | |
| 2014/0309600 A1 | 10/2014 | Aceto et al. | |
| 2014/0323909 A1 | 10/2014 | Kim | |
| 2014/0327433 A1 | 11/2014 | Anway et al. | |
| 2014/0336493 A1 | 11/2014 | Kulach et al. | |
| 2015/0057634 A1 | 2/2015 | Mastrototaro et al. | |
| 2015/0150457 A1 | 6/2015 | Wu et al. | |
| 2015/0151051 A1 | 6/2015 | Tsoukalis | |
| 2015/0230706 A1 | 8/2015 | Nakagawa et al. | |
| 2015/0231802 A1 | 8/2015 | Quan et al. | |
| 2015/0250639 A1 | 9/2015 | Thirstrup et al. | |
| 2015/0257923 A1 | 9/2015 | Thirstrup et al. | |
| 2015/0272495 A1 | 10/2015 | Greener | |
| 2015/0328389 A1 | 11/2015 | Heppe | |
| 2015/0342777 A1 | 12/2015 | Seres et al. | |
| 2015/0351690 A1 | 12/2015 | Toth et al. | |
| 2015/0374896 A1 | 12/2015 | Du et al. | |
| 2016/0008182 A1 | 1/2016 | Prokopuk et al. | |
| 2016/0015570 A1 | 1/2016 | Heinecke et al. | |

(56) References Cited

U.S. PATENT DOCUMENTS

| | | |
|---|---|---|
| 2016/0058604 A1 | 3/2016 | Wiltshire et al. |
| 2016/0084869 A1 | 3/2016 | Yuen et al. |
| 2016/0103966 A1 | 4/2016 | Mirza |
| 2016/0117062 A1 | 4/2016 | Hussam et al. |
| 2016/0158056 A1 | 6/2016 | Davis et al. |
| 2016/0158517 A1 | 6/2016 | Nebbia |
| 2016/0158969 A1 | 6/2016 | McLane et al. |
| 2016/0166438 A1 | 6/2016 | Rovaniemi |
| 2016/0178387 A1 | 6/2016 | Yamasaki et al. |
| 2016/0198996 A1 | 7/2016 | Dullen |
| 2016/0218555 A1 | 7/2016 | Slaby et al. |
| 2016/0235581 A1 | 8/2016 | Keleny et al. |
| 2016/0235582 A1 | 8/2016 | Moavenian |
| 2016/0242654 A1 | 8/2016 | Quinlan et al. |
| 2016/0278990 A1 | 9/2016 | Chen |
| 2016/0284084 A1 | 9/2016 | Gurcan et al. |
| 2016/0305776 A1 | 10/2016 | Mårtensson et al. |
| 2016/0310077 A1 | 10/2016 | Hunter et al. |
| 2016/0310140 A1 | 10/2016 | Belson et al. |
| 2016/0310329 A1 | 10/2016 | Patel et al. |
| 2016/0317728 A1 | 11/2016 | Lewis et al. |
| 2016/0331232 A1 | 11/2016 | Love et al. |
| 2016/0331235 A1 | 11/2016 | Nyberg et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079530 A1 | 3/2017 | DiMaio et al. |
| 2017/0079576 A1 | 3/2017 | Stroebech et al. |
| 2017/0090236 A1 | 3/2017 | Yeh et al. |
| 2017/0098044 A1 | 4/2017 | Lai et al. |
| 2017/0112658 A1 | 4/2017 | Hosono |
| 2017/0113001 A1 | 4/2017 | Trock |
| 2017/0140103 A1* | 5/2017 | Angelides ............ A61F 5/4404 |
| 2017/0156920 A1 | 6/2017 | Hunt et al. |
| 2017/0181628 A1 | 6/2017 | Burnette et al. |
| 2017/0262986 A1 | 9/2017 | Xiong et al. |
| 2017/0319073 A1 | 11/2017 | DiMaio et al. |
| 2017/0340474 A1* | 11/2017 | Thirstrup ............... A61B 5/746 |
| 2017/0340498 A1 | 11/2017 | Tessmer et al. |
| 2017/0348137 A1* | 12/2017 | Hvid ................ A61M 3/0295 |
| 2017/0360592 A1* | 12/2017 | Carrubba ............... A61F 5/445 |
| 2017/0360593 A1 | 12/2017 | Cox |
| 2018/0021164 A1 | 1/2018 | Fenton |
| 2018/0021165 A1 | 1/2018 | Fenton |
| 2018/0049667 A1 | 2/2018 | Heppe |
| 2018/0055359 A1 | 3/2018 | Shamim et al. |
| 2018/0078163 A1 | 3/2018 | Welch |
| 2018/0109852 A1 | 4/2018 | Mandapaka et al. |
| 2018/0110078 A1 | 4/2018 | Mandapaka et al. |
| 2018/0136712 A1 | 5/2018 | Niikura et al. |
| 2018/0171183 A1 | 6/2018 | Sakurai et al. |
| 2018/0177626 A1 | 6/2018 | Israelson |
| 2018/0250156 A1 | 9/2018 | Lam |
| 2018/0298240 A1 | 10/2018 | Chatterjee et al. |
| 2018/0318475 A1 | 11/2018 | Thomson et al. |
| 2018/0344533 A1 | 12/2018 | Rovaniemi |
| 2019/0008439 A1 | 1/2019 | Sageder et al. |
| 2019/0099552 A1 | 4/2019 | Zhang et al. |
| 2019/0133810 A1 | 5/2019 | Seres et al. |
| 2019/0133811 A1* | 5/2019 | Seres ..................... A61B 5/445 |
| 2019/0133812 A1* | 5/2019 | Seres ..................... A61B 5/445 |
| 2019/0142623 A1* | 5/2019 | Schoess ................ A61F 5/443 |
| | | 604/336 |
| 2019/0175386 A1 | 6/2019 | Monty |
| 2019/0184093 A1 | 6/2019 | Sjolund et al. |
| 2019/0192066 A1 | 6/2019 | Schoess et al. |
| 2019/0192332 A1* | 6/2019 | Hansen ................ G08C 17/02 |
| 2019/0192333 A1 | 6/2019 | Hansen et al. |
| 2019/0192334 A1* | 6/2019 | Hansen ................ A61F 5/445 |
| 2019/0240059 A1 | 8/2019 | Seres et al. |
| 2019/0247050 A1 | 8/2019 | Goldsmith |
| 2019/0374163 A1 | 12/2019 | Faarbaek et al. |
| 2019/0374372 A1 | 12/2019 | Seres et al. |
| 2020/0100931 A1 | 4/2020 | Schoess et al. |
| 2020/0114535 A1 | 4/2020 | Wattam et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Muñoz Herencia |
| 2020/0279368 A1 | 9/2020 | Tada et al. |
| 2020/0297244 A1 | 9/2020 | Brownhill et al. |
| 2020/0306074 A1* | 10/2020 | Speiermann .......... A61F 5/4404 |
| 2020/0322793 A1 | 10/2020 | Yang |
| 2020/0330258 A1* | 10/2020 | Hansen ................. A61F 5/448 |
| 2020/0330260 A1* | 10/2020 | Hansen ............... A61B 5/4283 |
| 2020/0337880 A1* | 10/2020 | Hansen ................. A61F 5/443 |
| 2020/0337881 A1* | 10/2020 | Hansen ................ H04M 3/244 |
| 2020/0337882 A1* | 10/2020 | Hansen ................. A61F 5/448 |
| 2020/0337883 A1* | 10/2020 | Hansen ................. A61F 5/443 |
| 2020/0375499 A1* | 12/2020 | Hansen ............... A61B 5/4216 |
| 2020/0375782 A1* | 12/2020 | Hansen ................... G01M 3/40 |
| 2020/0375783 A1* | 12/2020 | Hansen ................ A61F 5/4404 |
| 2020/0375784 A1* | 12/2020 | Hansen ................. A61F 5/443 |
| 2020/0375785 A1* | 12/2020 | Hansen ................. G16H 30/40 |
| 2020/0375786 A1* | 12/2020 | Hansen ................ A61F 5/4404 |
| 2020/0375809 A1 | 12/2020 | Sullivan et al. |
| 2020/0383637 A1* | 12/2020 | Hansen ............... A61B 5/6832 |
| 2020/0383818 A1* | 12/2020 | Hansen ................... A61F 5/44 |
| 2020/0383819 A1* | 12/2020 | Sletten ................. A61F 5/445 |
| 2020/0383820 A1* | 12/2020 | Hansen ................ G16H 40/40 |
| 2020/0383821 A1* | 12/2020 | Hansen ................... A61F 5/44 |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1* | 1/2021 | Hansen ................. A61F 5/443 |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1* | 1/2021 | Hansen ................... A61F 5/44 |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1* | 3/2021 | Hansen ................. A61F 5/445 |
| 2021/0085512 A1* | 3/2021 | Hansen ............... A61B 5/4851 |
| 2021/0100533 A1 | 4/2021 | Seres et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1* | 11/2021 | Larsen ................... A61F 5/443 |
| 2021/0361465 A1 | 11/2021 | Hansen et al. |
| 2021/0361466 A1* | 11/2021 | Hansen ................. A61B 90/96 |
| 2021/0361467 A1* | 11/2021 | Hansen ................... A61F 5/44 |
| 2021/0369197 A1* | 12/2021 | Hansen ................ A61B 5/7435 |
| 2021/0369488 A1* | 12/2021 | Hansen ................ A61F 5/4404 |
| 2021/0369489 A1* | 12/2021 | Hansen ................. B29C 65/48 |
| 2021/0369490 A1* | 12/2021 | Hansen ................ A61F 5/4404 |
| 2021/0370217 A1 | 12/2021 | Kirschman |
| 2021/0386368 A1 | 12/2021 | Carlsson et al. |
| 2022/0000652 A1* | 1/2022 | Thirstrup ............... A61F 5/443 |
| 2022/0031227 A1 | 2/2022 | Cho et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0110585 A1 | 4/2022 | Andersen |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |

(56) References Cited

U.S. PATENT DOCUMENTS

| | | |
|---|---|---|
| 2022/0265458 A1 | 8/2022 | Carlsson et al. |
| 2022/0378602 A1* | 12/2022 | Hansen .............. A61F 5/4404 |
| 2023/0059470 A1* | 2/2023 | Hansen .............. A61F 5/445 |
| 2023/0064734 A1* | 3/2023 | Hansen .............. A61F 5/443 |
| 2023/0105402 A1* | 4/2023 | Hansen .............. A61F 13/511 |
| | | 604/344 |
| 2023/0117727 A1* | 4/2023 | Hansen .............. G06T 7/70 |
| | | 604/327 |
| 2023/0118594 A1* | 4/2023 | Speiermann ...... A61B 5/150809 |
| | | 604/318 |
| 2023/0141297 A1 | 5/2023 | Herold et al. |
| 2023/0145670 A1 | 5/2023 | Seres et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |
| 2023/0329893 A1 | 10/2023 | Olsen et al. |
| 2023/0338005 A1 | 10/2023 | Barthe et al. |

FOREIGN PATENT DOCUMENTS

| | | |
|---|---|---|
| CA | 3009449 C | 9/2019 |
| CA | 3002372 C | 3/2021 |
| CA | 2947016 C | 2/2023 |
| CN | 203786580 U | 8/2014 |
| CN | 104902399 A | 9/2015 |
| CN | 104980878 A | 10/2015 |
| CN | 105588856 A | 5/2016 |
| CN | 206271160 U | 6/2017 |
| CN | 206450708 U | 8/2017 |
| CN | 107661167 A | 2/2018 |
| CN | 105615896 B | 5/2019 |
| CN | 105359167 B | 6/2019 |
| DE | 3437950 A1 | 4/1985 |
| DE | 3836590 A1 | 5/1990 |
| DE | 19900611 C1 | 7/2000 |
| DE | 69722993 | 7/2003 |
| DE | 102011014321 A1 | 9/2012 |
| DE | 102011076219 A1 | 11/2012 |
| EP | 0168967 A1 | 1/1986 |
| EP | 0373782 B1 | 10/1994 |
| EP | 0416397 B1 | 5/1995 |
| EP | 0800804 B1 | 6/2003 |
| EP | 1188157 B1 | 12/2005 |
| EP | 2108345 A1 | 10/2009 |
| EP | 1275357 B1 | 3/2011 |
| EP | 2000083 B1 | 8/2012 |
| EP | 2601915 A1 | 6/2013 |
| EP | 2738960 A1 | 6/2014 |
| EP | 2489561 B1 | 8/2014 |
| EP | 2453851 B1 | 10/2014 |
| EP | 2654646 B1 | 7/2016 |
| EP | 3213727 B1 | 12/2019 |
| EP | 3064179 B1 | 9/2021 |
| EP | 3226946 B1 | 8/2023 |
| GB | 2219679 A | 12/1989 |
| GB | 2308306 B | 9/1999 |
| GB | 2343628 B | 10/2000 |
| GB | 2465742 B | 7/2012 |
| GB | 2486968 B | 2/2015 |
| GB | 2542093 A | 3/2017 |
| GB | 2561193 B | 9/2020 |
| JP | H0474882 A | 3/1992 |
| JP | H06152077 A | 5/1994 |
| JP | H0910184 A | 1/1997 |
| JP | 2000093448 A | 4/2000 |
| JP | 2001087299 A | 4/2001 |
| JP | 2002055074 A | 2/2002 |
| JP | 2002224093 A | 8/2002 |
| JP | 2005323981 A | 11/2005 |
| JP | 2007319561 A | 12/2007 |
| JP | 2009519751 A | 5/2009 |
| JP | 2014033745 A | 2/2014 |
| JP | 2014054368 A | 3/2014 |
| KR | 101056989 B1 | 8/2011 |
| KR | 20120003987 A | 1/2012 |
| KR | 200485138 Y1 | 12/2017 |
| NL | 1001019 C2 | 2/1997 |
| NL | 1003904 C2 | 3/1998 |
| RU | 2527155 C2 | 8/2014 |
| TW | 201201783 A | 1/2012 |
| WO | 1994015562 A1 | 7/1994 |
| WO | 1997010012 A1 | 3/1997 |
| WO | 1999033037 A1 | 7/1999 |
| WO | 1999036017 A1 | 7/1999 |
| WO | 2000079497 A1 | 12/2000 |
| WO | 2001013830 A1 | 3/2001 |
| WO | 2001050996 A1 | 7/2001 |
| WO | 2002052302 A2 | 7/2002 |
| WO | 2002099765 A1 | 12/2002 |
| WO | 2005038693 A1 | 4/2005 |
| WO | 2005082271 A2 | 9/2005 |
| WO | 2006008866 A1 | 1/2006 |
| WO | 2006094513 A2 | 9/2006 |
| WO | 2007000168 A1 | 1/2007 |
| WO | 2007059774 A2 | 5/2007 |
| WO | 2007070266 A1 | 6/2007 |
| WO | 2007098762 A1 | 9/2007 |
| WO | 2007128038 A1 | 11/2007 |
| WO | 2007133555 A2 | 11/2007 |
| WO | 2008057884 A2 | 5/2008 |
| WO | 2009006900 A1 | 1/2009 |
| WO | 2009052496 A1 | 4/2009 |
| WO | 2009107011 A1 | 9/2009 |
| WO | 2009112912 A2 | 9/2009 |
| WO | 2011003420 A1 | 1/2011 |
| WO | 2011003421 A1 | 1/2011 |
| WO | 2011004165 A1 | 1/2011 |
| WO | 2011061540 A1 | 5/2011 |
| WO | 2011105701 A2 | 9/2011 |
| WO | 2011123018 A1 | 10/2011 |
| WO | 2011139499 A1 | 11/2011 |
| WO | 2011161254 A2 | 12/2011 |
| WO | 2012068386 A1 | 5/2012 |
| WO | 2012076022 A2 | 6/2012 |
| WO | 2012084987 A2 | 6/2012 |
| WO | 2013013197 A1 | 1/2013 |
| WO | 2013095231 A1 | 6/2013 |
| WO | 2013164517 A1 | 11/2013 |
| WO | 2014004207 A1 | 1/2014 |
| WO | 2014086369 A1 | 6/2014 |
| WO | 2014116816 A1 | 7/2014 |
| WO | 2015007284 A1 | 1/2015 |
| WO | 2015014774 A1 | 2/2015 |
| WO | 2015084462 A1 | 6/2015 |
| WO | 2015094064 A1 | 6/2015 |
| WO | 2015187366 A1 | 12/2015 |
| WO | 2016124202 A1 | 8/2016 |
| WO | 2016132738 A1 | 8/2016 |
| WO | 2016162038 A1 | 10/2016 |
| WO | 2016166731 A1 | 10/2016 |
| WO | 2016192738 A1 | 12/2016 |
| WO | 2017023794 A1 | 2/2017 |
| WO | 2017062042 A1 | 4/2017 |
| WO | 2017067558 A1 | 4/2017 |
| WO | 2017067560 A1 | 4/2017 |
| WO | 2017074505 A1 | 5/2017 |
| WO | 2017088153 A1 | 6/2017 |
| WO | 2017108109 A1 | 6/2017 |
| WO | 2017136696 A1 | 8/2017 |
| WO | 2017190752 A1 | 11/2017 |
| WO | 2018028756 A1 | 2/2018 |
| WO | 2019094635 A1 | 5/2019 |
| WO | 2019120432 A1 | 6/2019 |
| WO | 2019161859 A1 | 8/2019 |
| WO | 2019161860 A1 | 8/2019 |
| WO | 2019161863 A1 | 8/2019 |
| WO | 2019174693 A1 | 9/2019 |
| WO | 2019174695 A1 | 9/2019 |
| WO | 2019213623 A1 | 11/2019 |
| WO | 2020035121 A1 | 2/2020 |

* cited by examiner

METHOD OF MONITORING PERFORMANCE OF AN OSTOMY DEVICE WITH A MONITOR DEVICE ATTACHABLE TO BOTH AN OSTOMY APPLIANCE AND AN ACCESSORY DEVICE

The present disclosure relates to an ostomy system, devices thereof and method for monitoring an ostomy appliance. The ostomy appliance system comprises an ostomy appliance and an ostomy monitor device. In particular, the present disclosure relates to leakage classification and/or detection and monitoring of the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
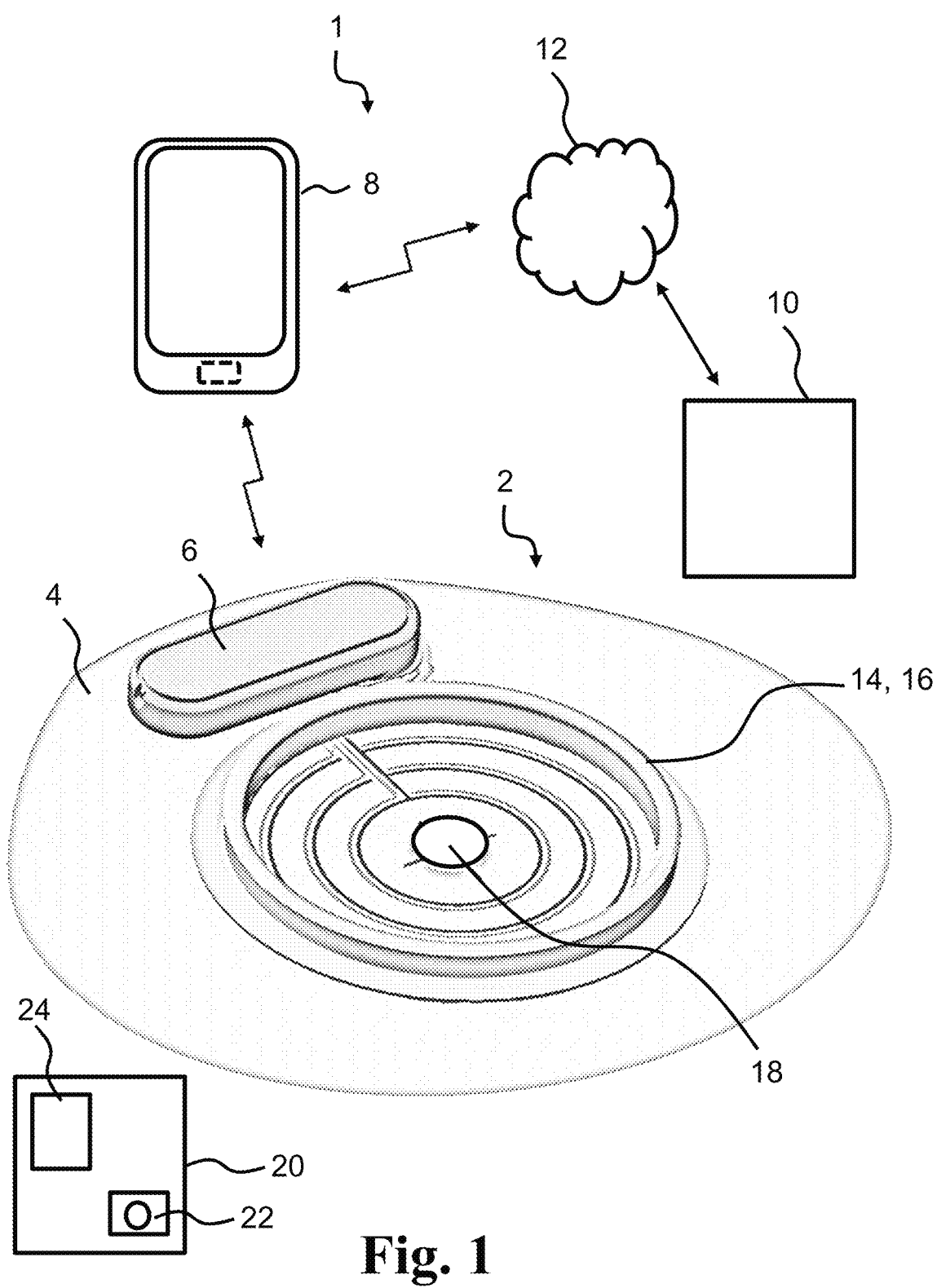
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

The base plate and/or the sensor assembly part may comprise a first adhesive layer, also denoted centre adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer may have a stomal opening, such as a first adhesive stomal opening, with a centre point.

The first adhesive layer may be made of a first composition. The first composition may comprise one or more polyisobutenes and/or styrene-isoprene-styrene. The first composition may comprise one or more hydrocolloids.

The first composition may be a pressure sensitive adhesive composition suitable for medical purposes comprising a rubbery elastomeric base and one or more water soluble or water swellable hydrocolloids. The first composition may comprise one or more water soluble or water swellable hydrocolloids.

The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethylcellulose (CMC). The first composition may optionally contain other components, such as fillers, tackifiers, plasticizers, and other additives The first adhesive layer may have a plurality of sensor point openings. A sensor point opening of the first adhesive layer is optionally configured to overlap a part of an electrode, e.g. to form a sensor point. The sensor point openings of the first adhesive layer may comprise primary sensor point openings.

The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm.

The first adhesive layer may have a primary thickness in a primary part of the first adhesive layer, e.g. in a primary region within a primary radial distance or in a primary radial distance range from the centre point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the centre point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be an adhesive layer, also denoted rim adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a centre point.

The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethylcellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly, such as the support layer of the electrode assembly, may have a stomal opening, such as an electrode assembly stomal opening and/or a support layer stomal opening, with a centre point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly may comprise a masking element configured to insulate at least parts of the electrodes from the first adhesive layer of the base plate and/or the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. The masking element may comprise polymeric (e.g. polyurethane, PTFE, PVDF) and/or ceramic (e.g. alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyamide, polyimide, Ethylene-vinyl acetate (EVA), polyurea, and silicones.

Exemplary thermoplastic elastomers of the masking element are styrenic block copolymers (TPS, TPE-s), thermoplastic polyolefinelastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate on the skin. The release liner may have a stomal opening, such as a release liner stomal opening, with a centre point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening, such as a top layer stomal opening, with a centre point. The top layer may have a thickness in the range from 0.01 mm to 1.0 mm, e.g. in the range from 0.02 mm to 0.2 mm, such as 0.04 mm.

The base plate and/or the sensor assembly part comprises a monitor interface. The monitor interface may be configured for electrically and/or mechanically connecting the ostomy appliance (base plate/sensor assembly part) to the monitor device. The monitor interface may be configured for wirelessly connecting the ostomy appliance (base plate/sensor assembly part) to the monitor device. Thus, the monitor interface of the base plate and/or the sensor assembly part is configured to electrically and/or mechanically couple the ostomy appliance and the monitor device.

The monitor interface of the base plate and/or the sensor assembly part may comprise, e.g. as part of a first connector of the monitor interface, a coupling part for forming a mechanical connection, such as a releasable coupling between the monitor device and the base plate and/or the sensor assembly part. The coupling part may be configured to engage with a coupling part of the monitor device for releasably coupling the monitor device to the base plate and/or the sensor assembly part. The coupling part of the base plate and/or the sensor assembly part may be denoted a base plate coupling part.

The monitor interface of the base plate and/or the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate and/or the sensor assembly part, such as of the electrode assembly. The first intermediate element may be arranged between the terminal elements and the first adhesive layer. The first intermediate element may cover or overlap terminal element(s) of the base plate and/or the sensor assembly part when seen in the axial direction. Thus, the first adhesive layer may be protected or experience more evenly distributed mechanical stress from the terminal elements of the base plate and/or the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or the sensor assembly part.

The base plate may comprise a coupling ring or other coupling member for coupling an ostomy pouch to the base plate (two-part ostomy appliance). The centre point maybe defined as a centre of the coupling ring.

The base plate and/or the sensor assembly part may have a stomal opening, e.g. with a centre point. The stomal opening of the base plate and/or the sensor assembly part may be formed collectively of stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part. The stomal opening may be a through-going passage of the base plate and/or the sensor assembly part. The stomal opening may be arranged substantially in the centre of the base plate and/or the sensor assembly part. The stomal opening(s) of the layers of the base plate and/or the sensor assembly part may be arranged substantially in the centre of the respective layer. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from a proximal side of the base plate and/or sensor assembly part to a distal side of the base plate and/or sensor assembly part.

The size and/or shape of the stomal opening may typically be adjusted by the user or nurse before application of the ostomy appliance to accommodate the user's stoma. In one or more exemplary base plates and/or sensor assembly parts, the user forms the stomal opening during preparation of the base plate and/or sensor assembly part for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate and/or the sensor assembly part, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate and/or the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate and/or the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by
($P\_1\_1 < TH\_1\_1$),
($P\_2\_1 > TH\_1\_2$), and
($P\_3\_1 > TH\_1\_3$),
wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion on the base plate and/or the sensor assembly part. The first threshold values ($TH\_1\_1$, $TH\_1\_2$ and $TH\_1\_3$) may be the same or different, e.g. depending on the electrode configuration of the base plate and/or the sensor assembly part. The first tertiary criterion ($P\_3\_1 < TH\_1\_3$) may be omitted in the first criteria set. The first primary parameter $P\_1\_1$ may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by
($P\_1\_1 < TH\_2\_1$),
($P\_2\_1 < TH\_2\_2$), and
($P\_3\_1 > TH\_2\_3$)
wherein $P\_1\_1$ is a first primary parameter based on the first parameter data and indicative of the resistance between the first electrode pair, $TH\_2\_1$ is a second primary threshold value, $P\_2\_1$ is a second primary parameter based on the second parameter data and indicative of the resistance between the second electrode pair, $TH\_2\_2$ is a second secondary threshold value, $P\_3\_1$ is a third primary parameter based on the third parameter data and indicative of the resistance between the third electrode pair, $TH\_2\_3$ is a second tertiary threshold value, and wherein the second operating state is indicative of medium degree of radial erosion on the base plate and/or the sensor assembly part. The second threshold values ($TH\_2\_1$, $TH\_2\_2$ and $TH\_2\_3$) may be the same or different, e.g. depending on the electrode configuration of the base plate and/or the sensor assembly part. The second primary criterion ($P\_1\_1 < TH\_2\_1$) and/or the second tertiary criterion ($P\_3\_1 > TH\_2\_3$) may be omitted in the second criteria set.

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by
($P\_1\_1 > TH\_D\_1$),
($P\_2\_1 > TH\_D\_2$), and
($P\_3\_1 > TH\_D\_3$)

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate and/or the sensor assembly part. The default threshold values (TH_D_1, TH_D_2 and TH_D_3) may be the same or different, e.g. depending on the electrode configuration of the base plate and/or the sensor assembly part. In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate and/or the sensor assembly part has experienced a third degree of radial erosion, e.g. the first adhesive layer is eroded to the third radial distance of the third electrode pair.

The third criteria set may be given by
(P_1_1<TH_3_1),
(P_2_1<TH_3_2), and
(P_3_1<TH_3_3)
wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate and/or the sensor assembly part. The third threshold values (TH_3_1, TH_3_2 and TH_3_3) may be the same or different, e.g. depending on the electrode configuration of the base plate and/or the sensor assembly part. The third primary criterion (P_1_1<TH_3_1) and/or the third secondary criterion (P_2_1<TH_3_2) may be omitted in the third criteria set.

In one or more exemplary monitor devices, the ostomy data comprises fourth ostomy data from a fourth electrode pair of the base plate and/or the sensor assembly part. To apply a processing scheme may comprise to obtain fourth parameter data based on the fourth ostomy data and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by
(P_4_1<TH_4_4)
wherein P_4_1 is a fourth primary parameter based on the fourth parameter data and indicative of the resistance between the fourth electrode pair and TH_4_4 is a fourth quaternary threshold value, and wherein the fourth operating state is indicative of high risk of leakage from the ostomy appliance. The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and//or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals (alternatively denoted monitor terminals), such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate and/or the sensor assembly part. The coupling part and the terminals of the first interface form (at least part of) a first connector of the monitor device. The coupling part of the monitor device may be denoted a monitor coupling part.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate and/or the sensor assembly part of the ostomy appliance.

The ostomy system may comprise a docking station including and/or forming an accessory device of the ostomy system. The docking station may be configured to be electrically and/or mechanically coupled to the monitor device.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station. The coupling part of an accessory device, such as the docking station may be denoted an accessory coupling part and/or a docking station coupling part.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

This disclosure relates to a monitor device for an ostomy system, such as the monitor device as described above. Also disclosed is an ostomy system comprising the disclosed monitor device and an accessory device, such as a docking device, and a base plate. The base plate may be a base plate comprising an applied sensor assembly part.

The monitor device may comprise a housing, such as a monitor device housing.

The monitor device may comprise a power unit e.g., disposed in the housing.

The monitor device may comprise a processor e.g., disposed in the housing.

The monitor device may comprise a first interface. The first interface may be configured to couple the monitor device, e.g. selectively, to a base plate of the ostomy system and/or an accessory device of the ostomy system.

The first interface may comprise a plurality of monitor terminals, e.g. configured to electrically couple the monitor device to the base plate and/or the accessory device, e.g., through a wired or wireless connection.

The first interface may comprise a coupling part, such as a monitor coupling part, e.g., configured to couple, such as releasably and structurally couple, the monitor device to, e.g. selectively, the base plate and/or the accessory device.

The base plate may comprise a base plate coupling part for forming a mechanical connection between the monitor device and the base plate. The accessory device may comprise an accessory coupling part for forming a mechanical connection between the monitor device and the docking station. The base plate coupling part may have the same shape and/or size as the accessory coupling part. Thereby a correspondingly shaped monitor coupling part may be allowed to engage with both the accessory coupling part and the base plate coupling part and may additionally be prevented from being engaged with both simultaneously.

The plurality of monitor terminals may include a primary terminal and a secondary terminal. The primary terminal may be any one of the ground terminal, the first terminal, the second terminal, the third terminal, the fourth terminal, the fifth terminal or the sixth terminal of the monitor device as described above. The secondary terminal may be any other one of the ground terminal, the first terminal, the second terminal, the third terminal, the fourth terminal, the fifth terminal or the sixth terminal of the monitor device as described above.

The primary terminal may be configured to form electrical connection with a primary electrode of the base plate when the monitor device is coupled to the base plate. The primary terminal may be configured to form electrical connection with a primary charge terminal of the accessory device when the monitor device is coupled to the accessory device.

The secondary terminal may be configured to form electrical connection with a secondary electrode of the base plate when the monitor device is coupled to the base plate. The secondary terminal may be configured to form electrical connection with a secondary charge terminal of the accessory device when the monitor device is coupled to the accessory device.

The primary electrode of the base plate may be any one of the ground electrode, the first electrode, the second electrode, the third electrode, the fourth electrode, the fifth electrode or the sixth electrode of the base plate as described above. The secondary electrode of the base plate may be any other one of the ground electrode, the first electrode, the second electrode, the third electrode, the fourth electrode, the fifth electrode or the sixth electrode.

The primary charge terminal of the accessory device may be any one of the ground terminal, the first terminal, the second terminal, the third terminal, the fourth terminal, the fifth terminal or the sixth terminal of the accessory device as described above. The secondary charge terminal of the accessory device may be any other one of the ground terminal, the first terminal, the second terminal, the third terminal, the fourth terminal, the fifth terminal or the sixth terminal. The primary charge terminal may be a terminal having a positive voltage potential, while the secondary charge terminal may form a ground or reference terminal.

For example, the primary charge terminal may be configured to have a voltage potential of +5V or +10V and the secondary charge terminal may be configured to have a voltage potential of 0V.

The processor may be configured to receive first ostomy data from the primary terminal and the secondary terminal, e.g. when the monitor device is coupled to the base plate. For example, the first ostomy data may be indicative of resistance between the primary terminal and the secondary terminal.

The plurality of monitor terminals may include a tertiary terminal and/or a quaternary terminal. The tertiary terminal may be any one of the ground terminal, the first terminal, the second terminal, the third terminal, the fourth terminal, the fifth terminal or the sixth terminal of the monitor device as described above. The quaternary terminal may be any other one of the ground terminal, the first terminal, the second terminal, the third terminal, the fourth terminal, the fifth terminal or the sixth terminal of the monitor device as described above.

The tertiary terminal may be configured to form electrical connection with a tertiary electrode of the base plate when the monitor device is coupled to the base plate. The tertiary terminal may be configured to form electrical connection with a primary data terminal of the accessory device when the monitor device is coupled to the accessory device.

The quaternary terminal may be configured to form electrical connection with a quaternary electrode of the base plate when the monitor device is coupled to the base plate. The quaternary terminal may be configured to form electrical connection with a secondary data terminal of the accessory device when the monitor device is coupled to the accessory device.

Under measuring conditions, the terminals used for charging may be influenced by charging components such that resistance between the respective terminals is reduced. Therefore, it may be advantageous to use terminals for charging, which during measuring are used for leakage detection, e.g. terminals for connecting with the ground electrode, the fourth electrode and/or the fifth electrode of the base plate, as described previously, because the measurements performed using these terminals are less influenced by the possible reduced resistance caused by charging components. Therefore, in an exemplary monitor device, one of the primary terminal and the secondary terminal is be configured to form electrical connection with an electrode of the base plate configured to detect leakage, such as the ground electrode, the fourth electrode or the fifth electrode, and the other of the primary terminal and the secondary terminal is configured to form electrical connection with another of the electrodes of the base plate configured to detect leakage. For example, the primary terminal may be configured to form electrical connection with the ground electrode of the base plate, and the secondary terminal may be configured to form electrical connection with the fourth electrode of the base plate. In another example, the primary terminal may be configured to form electrical connection with the ground electrode of the base plate, and the secondary terminal may be configured to form electrical connection with the fifth electrode of the base plate. In another example, the primary terminal may be configured to form electrical connection with the fourth electrode of the base plate, and the secondary terminal may be configured to form electrical connection with the ground electrode of the base plate. In another example, the primary terminal may be configured to form electrical connection with the fourth electrode of the base plate, and the secondary terminal may be configured to form electrical connection with the fifth electrode of the base plate. In another example, the primary terminal may be configured to form electrical connection with the fifth electrode of the base plate, and the secondary terminal may be configured to form electrical connection with the ground electrode of the base plate. In another example, the primary terminal may be configured to form electrical connection with the fifth electrode of the base plate, and the secondary terminal may be configured to form electrical connection with the fourth electrode of the base plate.

The monitor device, such as the processor of the monitor device, may be configured to exchange data between the monitor device and the accessory device, via the tertiary terminal and the quaternary terminal when the monitor device is coupled to the accessory device.

The processor may be configured to receive second ostomy data from the tertiary terminal and the quaternary terminal, e.g. when the monitor device is coupled to the base plate. For example, the second ostomy data may be indicative of resistance between the tertiary terminal and the quaternary terminal.

The power unit may comprise a battery and a charging circuit. The charging circuit may be connected to the battery and terminals, such as the primary terminal and/or the secondary terminal, of the first interface for charging the battery. The charging circuit may be configured to charge the battery from the first terminal and the second terminal, e.g. when the monitor device is coupled to the base plate. For example, the battery may be charged by a voltage difference between the first terminal and the second terminal.

The power unit may comprise a charging switch, such as a FET, transistor, or similar. The charging switch may be operable based on a voltage difference between the primary terminal and the secondary terminal. The charging-switch may be configured to electrically connect the primary terminal to a primary charging terminal of the charging circuit and/or to electrically connect the secondary terminal to a secondary charging terminal of the charging circuit when the voltage difference between the primary terminal and the secondary terminal is above a voltage threshold, such as 3V, such as 5V.

The charging-switch may be configured to electrically connect the primary terminal to the primary charging terminal by reducing the electrical resistance between the primary terminal and the primary charging terminal. Additionally or alternatively, the charging-switch may be configured to electrically connect the secondary terminal to the secondary charging terminal by reducing the electrical resistance between the secondary terminal and the secondary charging terminal.

Allowing the same interface, e.g., the first interface, to be used for connecting the monitor device to various devices, e.g., to the base plate and to the accessory device, may provide that simultaneous connection is prevented. Thereby, a connection from a building power outlet or plug to the user, wearing a base plate, may be effectively prevented.

Furthermore, by utilizing the same terminals for different purposes reduce the number of necessary terminals and thereby reduce complexity of the device as well as saves space and facilitates a smaller and more compact device.

The monitor device may enable information from the user and/or the docking station and/or about the base plate and/or its operation and/or status to be collected and transferred to one or more accessory devices.

The monitor device can be conveniently and effectively coupled to each of the one or more accessory devices. User experiences and efficacy can be enhanced. The terminals of the monitor device, base plate, docking station and any other accessory device can be configured for wired or wireless electrical connection and data exchange.

The first interface of the monitor device may be configured to couple the monitor device to the base plate to establish a monitor-to-base plate state. The first interface of the monitor device may be configured to couple to the docking station to establish a monitor-to-docking station state. For example, the processor can be configured to generate a monitor-to-base plate signal when the monitor device is coupled with the base plate. Alternatively or additionally, the processor may be configured to generate a monitor-to-docking station signal when the monitor device is coupled with the docking station. The monitor-to-base plate signal and/or monitor-to-docking station signal can, for example, be stored or logged in memory, either alone or with other data, thereby providing enhanced information about the use of the system.

The monitor coupling part of the monitor device can be configured to be releasably and structurally coupled to a base plate coupling part of the base plate. The monitor coupling part can be configured to be releasably and structurally coupled to a docking station coupling part of the docking station. The monitor coupling part can be configured to couple the monitor device to other accessory devices.

The plurality of monitor terminals of the monitor device can comprise a plurality of terminal elements, e.g. forming the plurality of monitor terminals.

The plurality of monitor terminals, such as the plurality of terminal elements, may include a first group of monitor terminals/terminal elements e.g., configured to electrically couple with the base plate. At least one of the first group of monitor terminals/terminal elements can be configured to transmit information from the base plate to the monitor device and/or transmit information from the monitor device to the base plate.

The plurality of monitor terminals/terminal elements can comprise a second group of monitor terminals/terminal elements configured to electrically couple with the accessory device. The second group of monitor terminals/terminal elements can be the same as or different than the first group of monitor terminals/terminal elements. At least one of the second group of monitor terminals/terminal elements can be configured to transmit electrical charge from the accessory device to the monitor device. For example, the power unit, e.g., comprising a battery, of the monitor device may be charged by the accessory device, e.g. via the at least one of the second group or monitor terminals/terminal elements. At least one of the second group of monitor terminals/terminal elements can be configured to transmit information from the monitor device to the accessory device and/or transmit information from the accessory device to the monitor device.

The monitor coupling part can comprise a first group of monitor magnetic members e.g. configured to be magnetically coupled to a group of base plate magnetic members of the base plate. The monitor coupling part can comprise a second group of monitor magnetic members e.g. configured to be magnetically coupled to a group of accessory magnetic members of the accessory device. Magnetic coupling by the magnetic members enables the components to be conveniently and effectively connected and disconnected during use.

The first group of monitor magnetic members can be configured to magnetically repel the group of accessory magnetic members. The second group of monitor magnetic members can be configured to magnetically repel the group of base plate magnetic members. For example, north-seeking poles of the first group of monitor magnetic members can be arranged in opposite direction compared to north-seeking poles of the second group of monitor magnetic members. This configuration of magnetic members may enable correct registration of the terminals of the monitor device and/or the terminals of the different devices (e.g., base plate, accessory device, etc.) to which it can be connected (i.e., the monitor device will correctly register to each different device, and the magnets will repel attempts to incorrectly register).

The power unit can comprise an energy storage member. The energy storage member(s) can include at least one of a primary battery, such as the battery as previously disclosed, a secondary battery, or a supercapacitor (e.g., two or more batteries). The energy storage member(s) may be rechargeable (e.g., though the accessory device station).

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate has a stoma-receiving opening 18 with a stoma centre point. The size and/or shape of the stomal opening 18 is typically adjusted by the user or nurse before application of the ostomy appliance to accommodate the user's stoma.

The ostomy system 1 optionally comprises a docking station 20 forming an accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
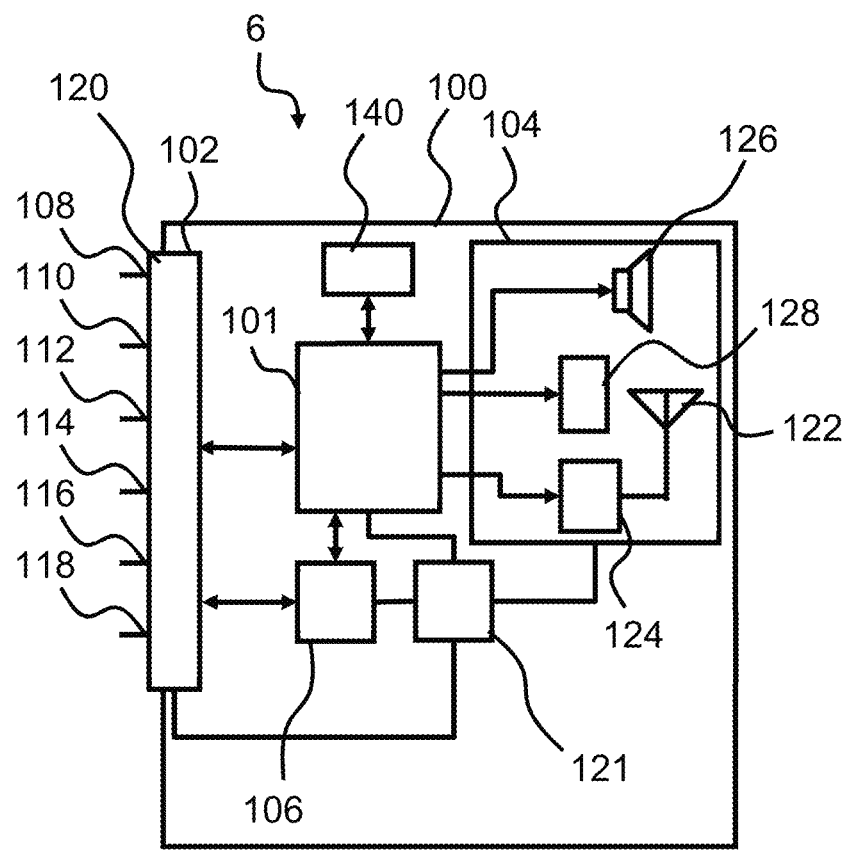
FIG. 2 illustrates an exemplary monitor device of the ostomy system.

FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector. The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 comprises a sensor unit 140 connected to the processor 101. The sensor unit 140 comprises a temperature sensor for feeding temperature data to the processor and a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

Figure 3:
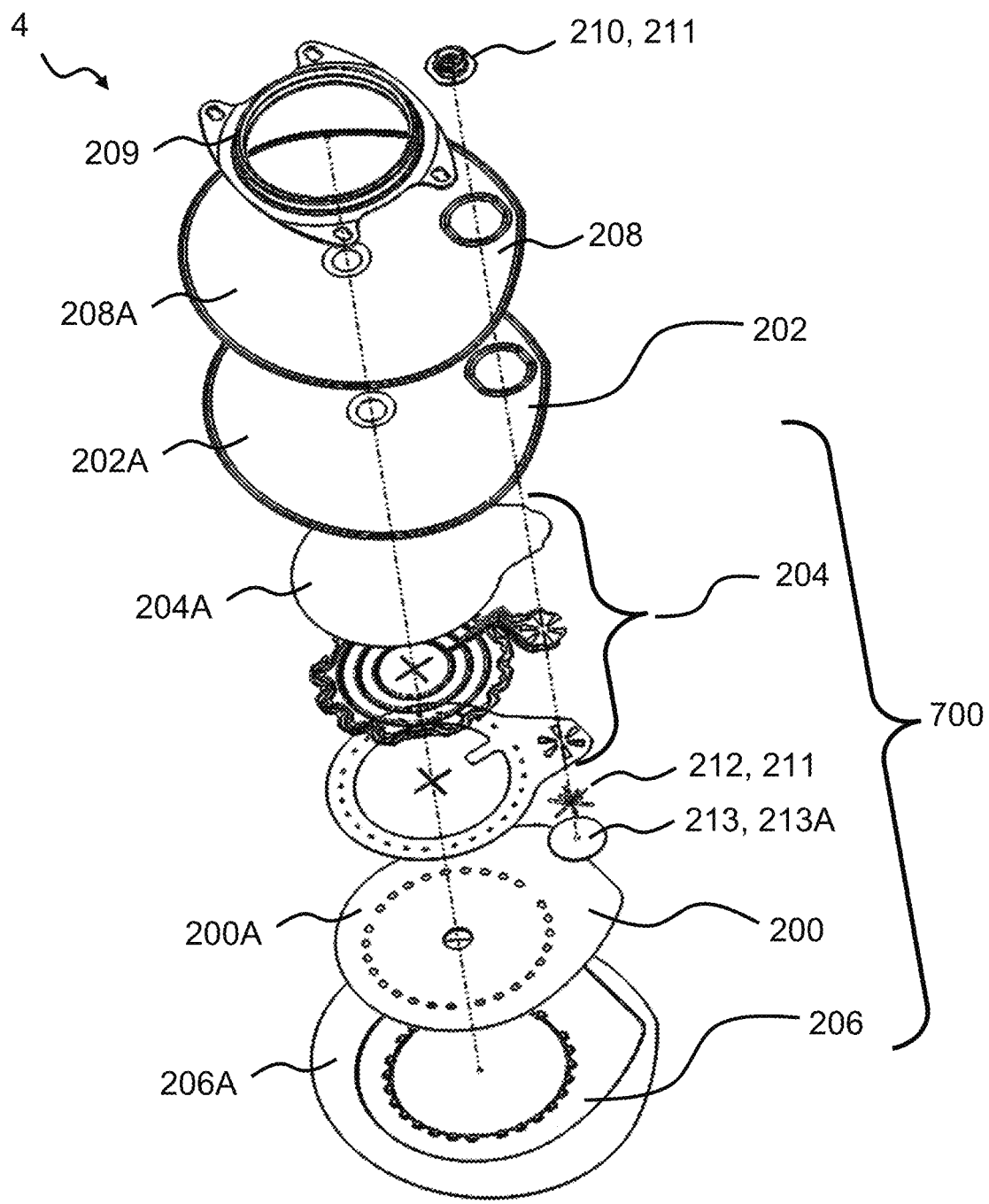
FIG. 3 is an exploded view of a base plate of an ostomy appliance.

FIG. 3 illustrates an exploded view of an exemplary base plate of an ostomy appliance. The base plate 4 comprises a first adhesive layer 200. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with electrodes formed on a proximal surface of the support layer. The base plate 4 comprises a release liner 206 that is peeled off by the user prior to applying the base plate 4 on the skin. The base plate 4 comprises a top layer 208 and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
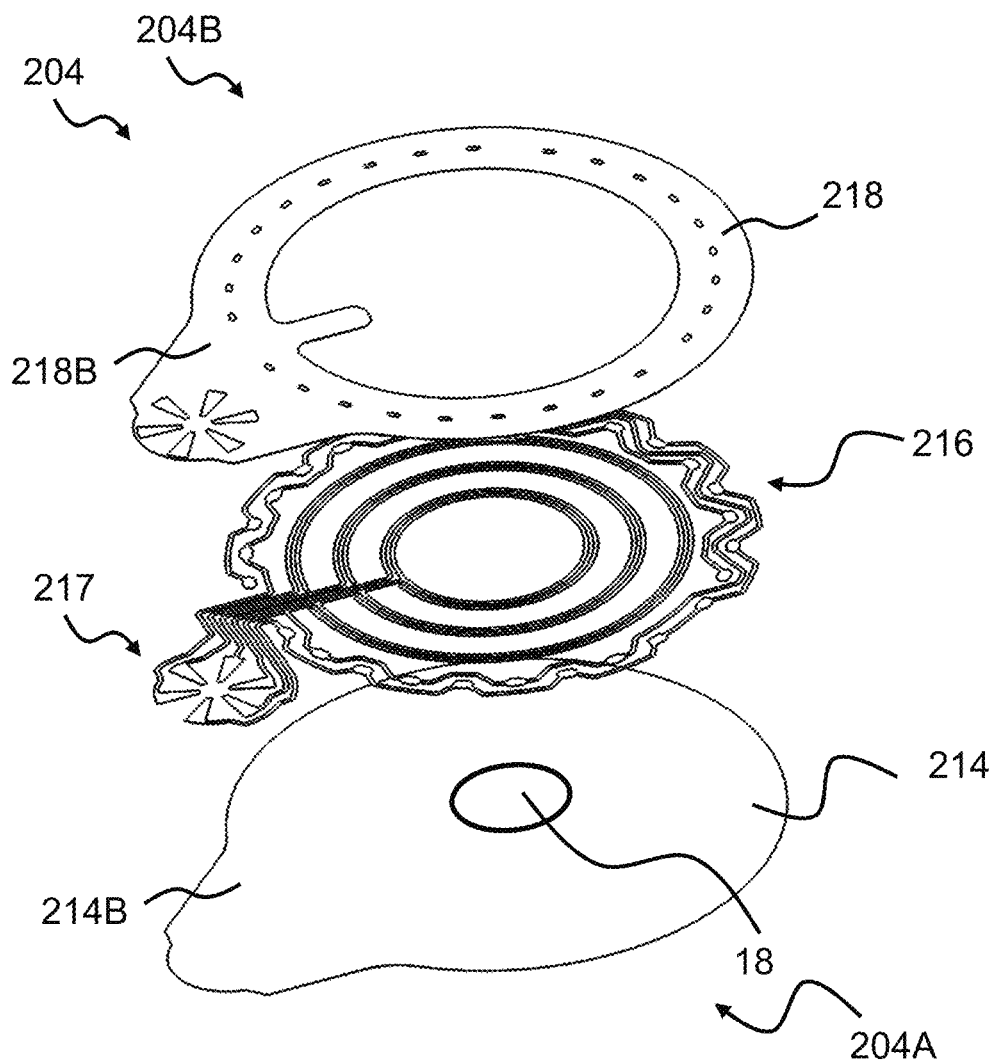
FIG. 4 is an exploded view of an exemplary electrode assembly.

FIG. 4 illustrates an exploded view of an exemplary electrode assembly 204 of a base plate and/or a sensor assembly part. The electrode assembly 204 has a distal side 204A and a proximal side 204B. The electrode assembly 204 comprises a support layer 214 with proximal side 214B and electrodes 216 arranged, such as formed, on the proximal side 214B of the support layer 214 and including a ground electrode, a first electrode, a second electrode, a third electrode, a fourth electrode, and a fifth electrode, wherein each electrode has a respective connection part for connecting the electrodes to respective terminal elements of the monitor interface. Further, electrode assembly 204 comprises a masking element 218 with proximal surface 218B and configured to insulate electrode parts of electrodes 216 from the first adhesive layer of the base plate and/or sensor assembly part. The masking element 218 covers or overlap with parts of the electrodes 216 when seen in the axial direction.

Figure 5:
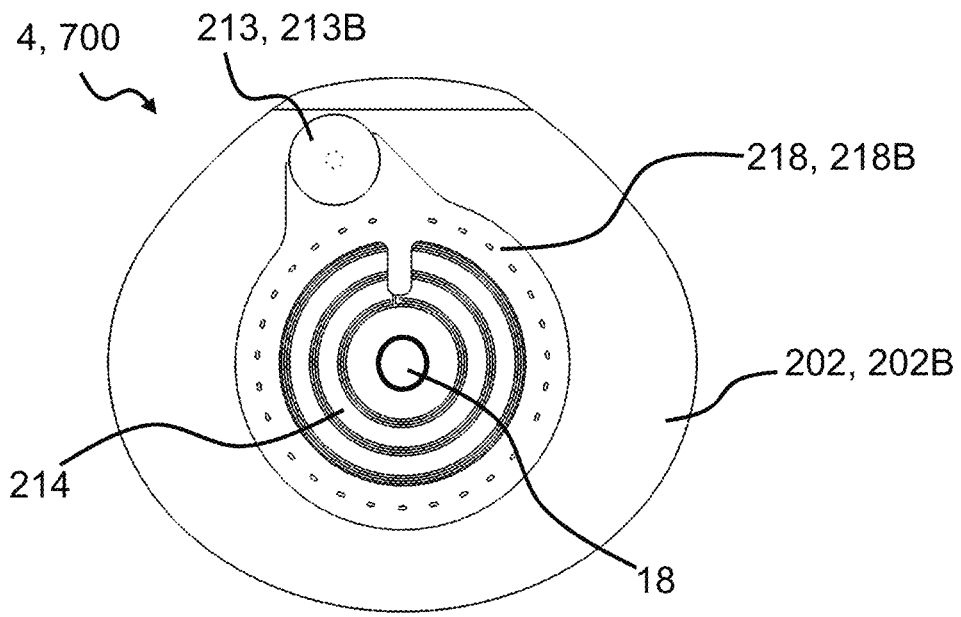
FIG. 5 is a proximal view of parts of a base plate and/or a sensor assembly part.

FIG. 5 is a proximal view of proximal surfaces of parts of the base plate and/or the sensor assembly part without the first adhesive layer and the release liner. The base plate 4 and/or the sensor assembly part 700 comprises a first intermediate element 213 on the proximal side of the electrode assembly, i.e. between the electrode assembly 204 and the first adhesive layer (not shown). The first intermediate element 213 covers the terminal elements of the base plate 4 and/or of the sensor assembly part 700 when seen in the axial direction and protects the first adhesive layer from mechanical stress from the terminal elements of the base plate and/or of the sensor assembly part.

Figure 6:
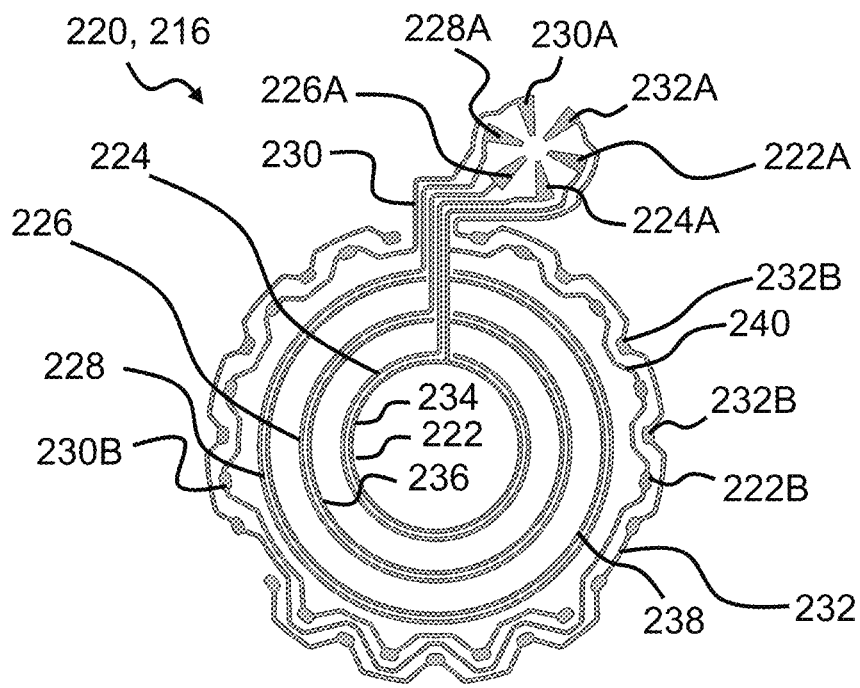
FIG. 6 is a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

Figure 7:
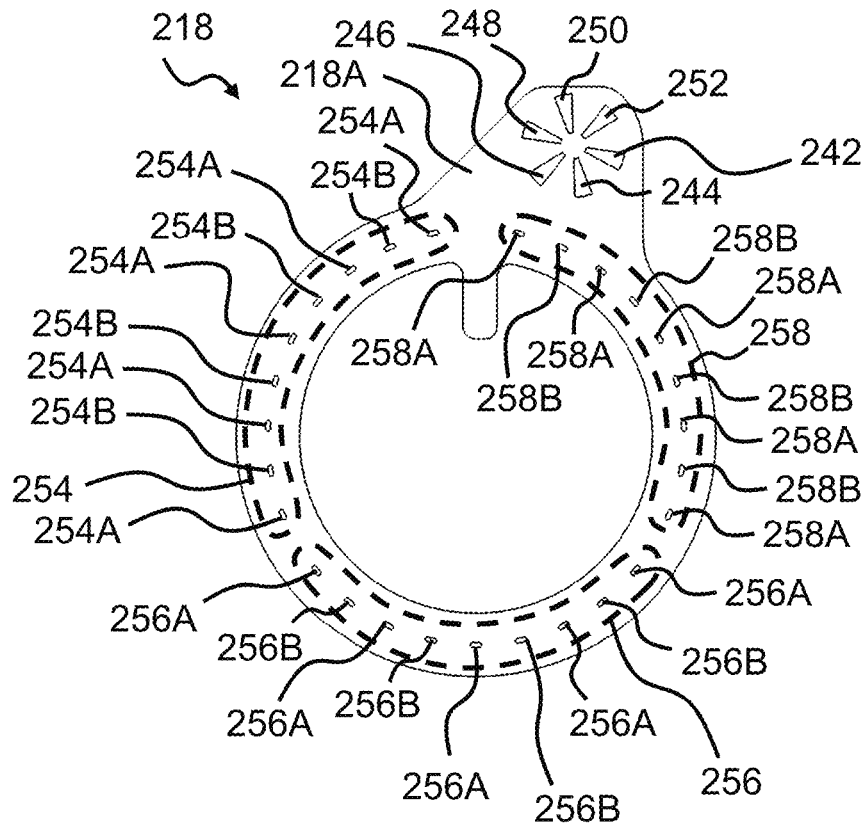
FIG. 7 is a distal view of an exemplary masking element.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
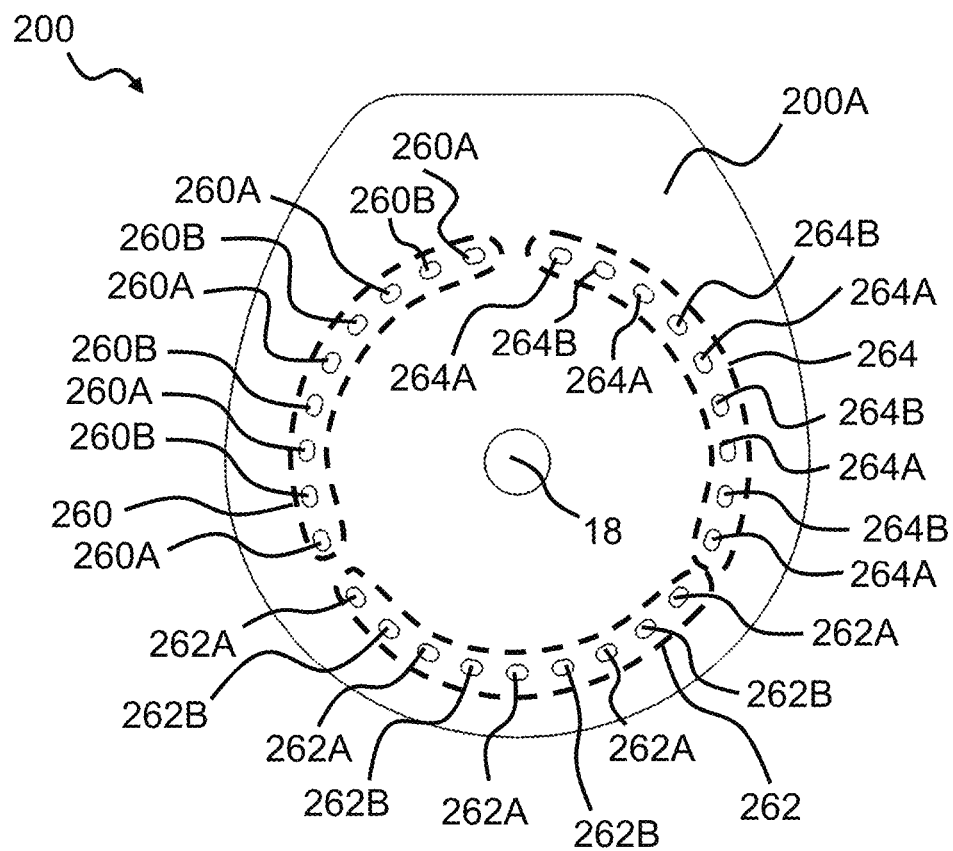
FIG. 8 is a distal view of an exemplary first adhesive layer.
Figure 9:
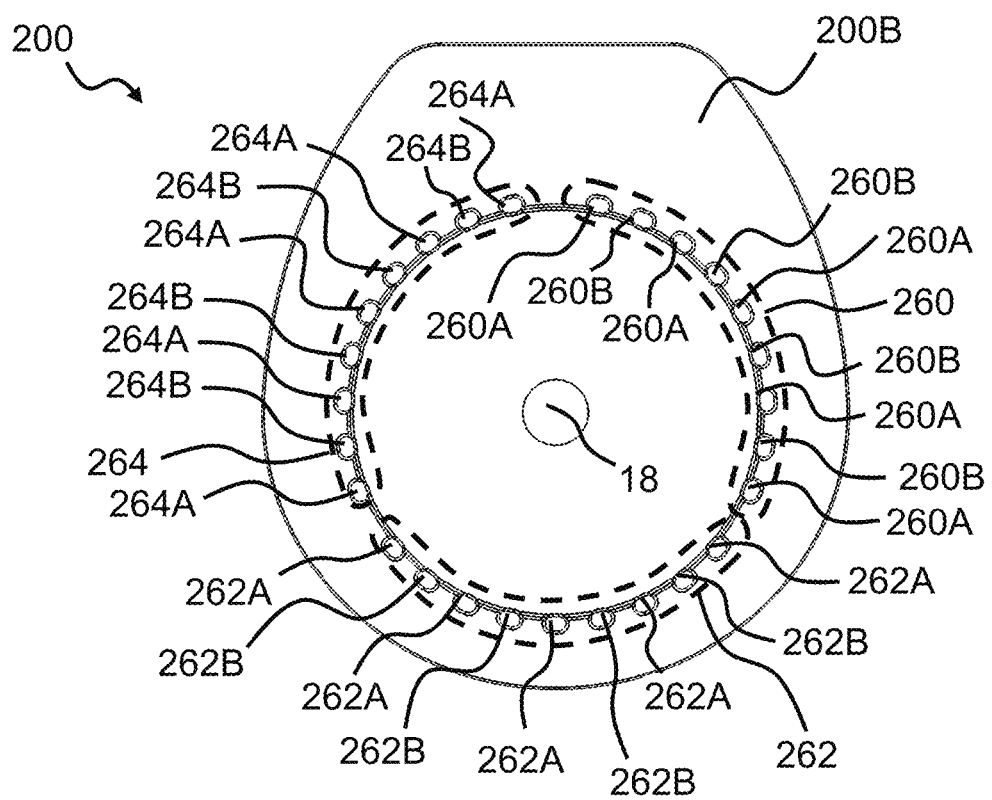
FIG. 9 is a proximal view of the first adhesive layer of FIG. 8.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232. The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
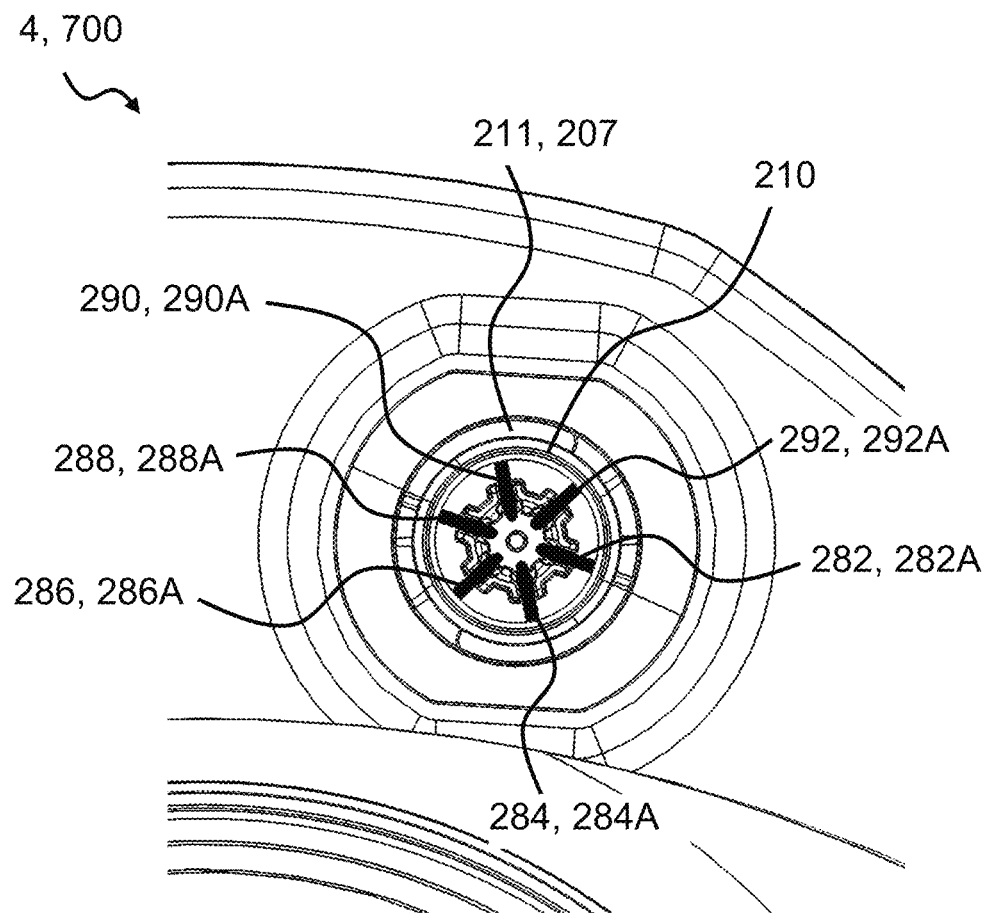
FIG. 10 is a distal view of a part of the base plate and/or sensor assembly part including a monitor interface.

FIG. 10 is a more detailed distal view of a part of the base plate 4 and/or the sensor assembly part 700. The base plate 4 and/or the sensor assembly part 700 comprises a monitor interface 207. The monitor interface 207 comprises the first connector 211. The first connector 211 comprises coupling part 210 configured to releasably couple the monitor device to the base plate 4 and/or the sensor assembly part 700 and thus forming a releasable coupling. The first connector 211 comprises a plurality of terminals formed by respective terminal elements for forming respective electrical connections with respective terminals of the monitor device.

The plurality of terminals of the first connector 211 of the monitor interface 207 comprises a ground terminal element 282 forming a ground terminal 282A, a first terminal element 284 forming a first terminal 284A, a second terminal element 286 forming a second terminal 286A, and a third terminal element 288 forming a third terminal 288A. The monitor interface 207 optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate and/or sensor assembly part, the number of terminals and the position of the terminals in the coupling part may be adapted to the electrode configuration used in the electrode assembly of the base plate and/or sensor assembly part.

Figure 11:
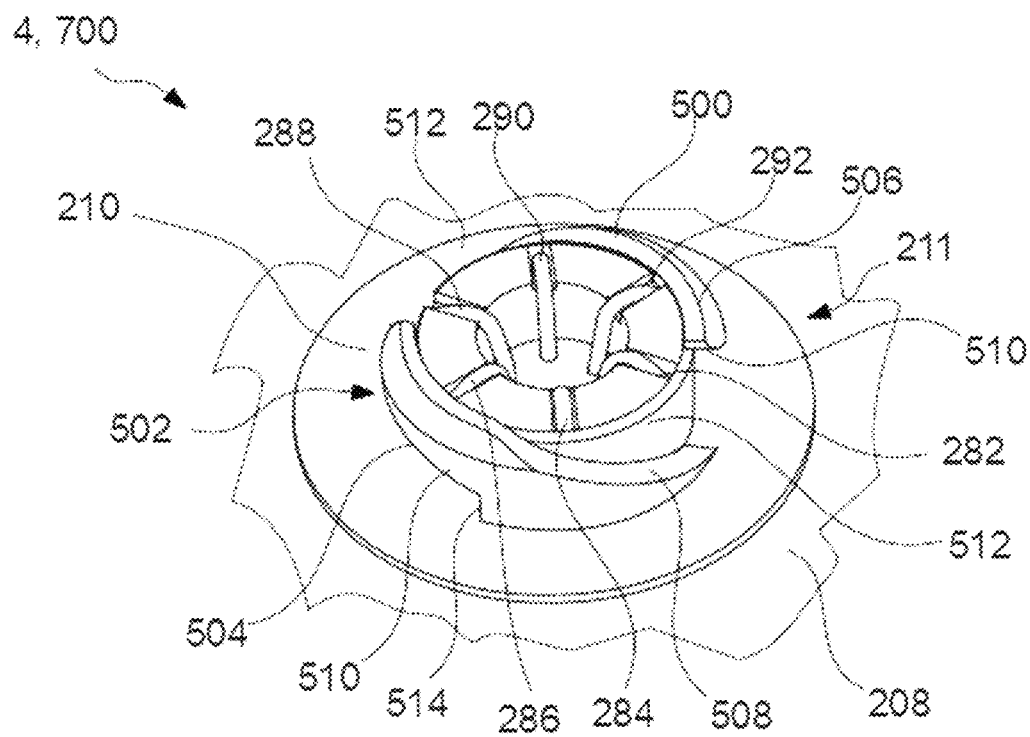
FIG. 11 is an isometric illustration of an exemplary monitor interface.

FIG. 11 is an isometric view of a part of a base plate 4 and/or sensor assembly part 700 including the first connector 211 of a monitor interface of the base plate 4 and/or sensor assembly part 700. As shown, the first connector 211 includes the coupling part 210 and terminal elements 282, 284, 286, 288, 290 and 292 forming respective terminals. The illustrated embodiment of the coupling part 210 includes a rim or post 500 that extends distally from the base plate 4 and/or sensor assembly part 700 and coupling threads 502 on a surface of the post 500 (e.g., on the outer surface in the illustrated embodiment). The threads 502 include one or more channels or slots 504 (two are shown in the illustrated embodiment) defined by projections 506 from the post 500. The protrusions or projections 506 have upper and lower surfaces 508 and 510, respectively. Each slot 504 has an upper opening 512 adjacent the top or distal end of the post 500, extending proximally toward the top layer 208 as it wraps in a circumferential direction around the post. Each slot 504 may have an end, e.g., defining a stop 514.

Terminal elements 282, 284, 286, 288, 290 and 292 are positioned at circumferentially spaced locations about the post 500. As described in greater detail below, the terminal elements 282, 284, 286, 288, 290 and 292 are located so as to contact one of the ground, first, second, third, fourth and fifth terminals 108, 110, 112, 114, 116 and 118, respectively, of the monitor device 6 (e.g., FIG. 2).

Figure 12:
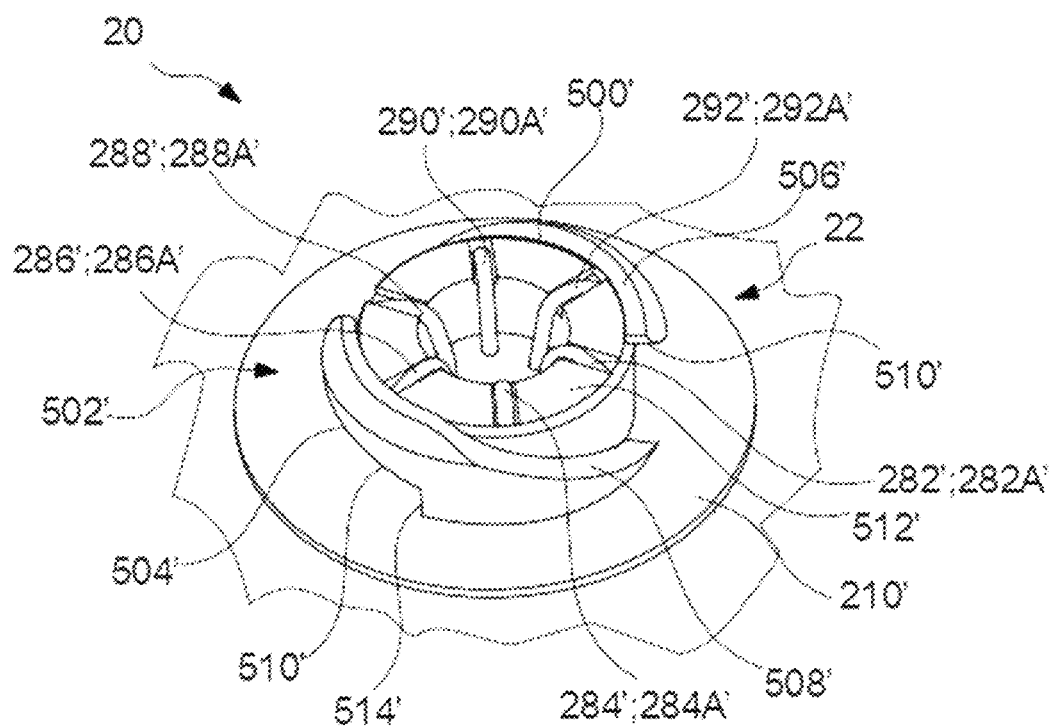
FIG. 12 is an isometric illustration of an exemplary docking monitor interface.

FIG. 12 is an isometric view of a part of an accessory device, such as the docking station 20 including the first connector 22 of the docking monitor interface of the docking station 20. In the illustrated embodiment, first connector 22 includes a coupling part 210' and terminal elements 282', 284', 286', 288', 290' and 292'. Ground terminal element 282' forms a ground terminal 282A'. First terminal element 284' forms a first terminal 284A'. Second terminal element 286' forms a second terminal 286A'. Third terminal element 288' forms a third terminal 288A'. Fourth terminal element 290' forms a fourth terminal 290A'. Fifth terminal element 292' forms a fifth terminal 292A'. Structural features of the first connector 22 can be substantially the same as or similar to those of the first connector 211 of the monitor interface of the base plate and/or sensor assembly part as described above. In embodiments, first connector 22 of the docking station 20 has more or fewer terminals and terminal elements than the first connector 211 of the monitor interface of the base plate and/or sensor assembly part.

Figure 13:
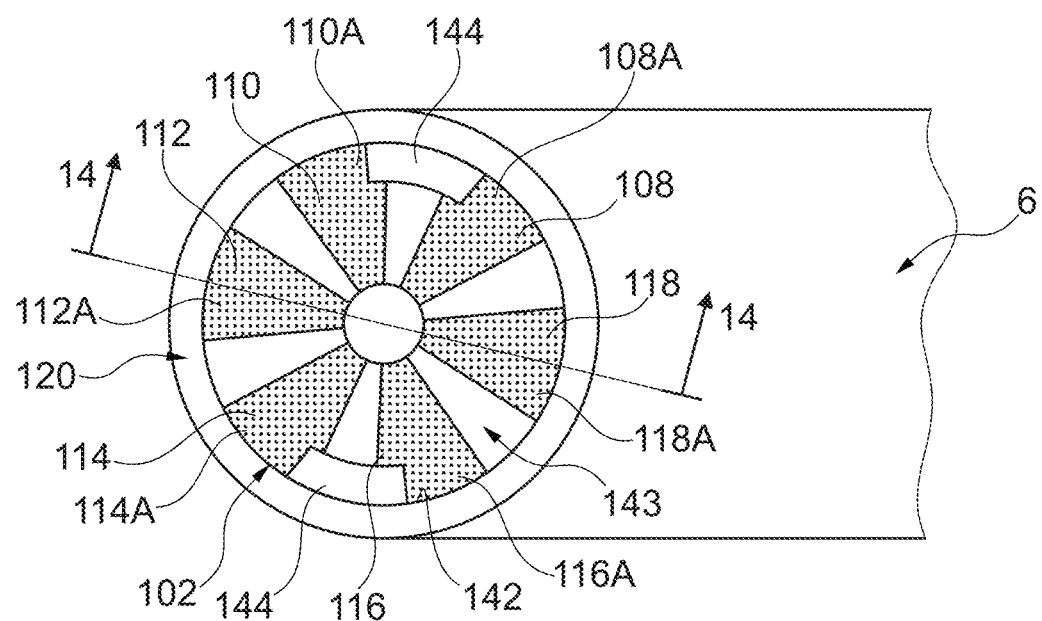
FIG. 13 is an illustration of a part of the monitor device.
Figure 14:
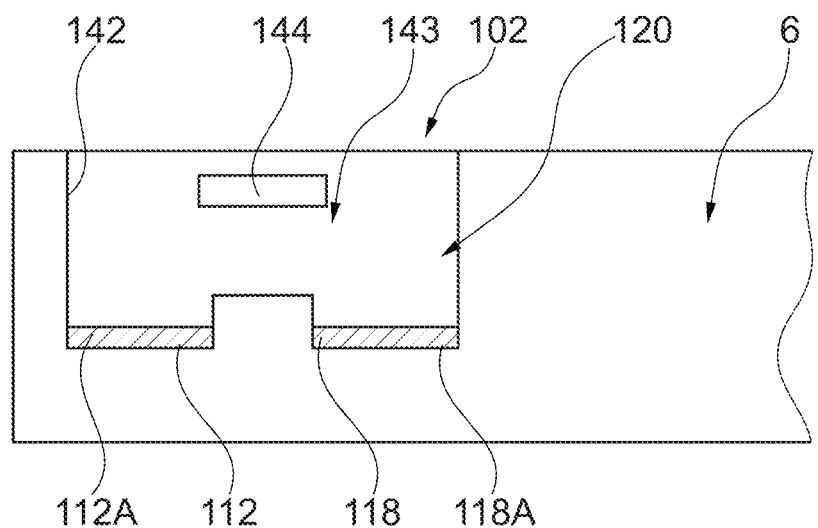
FIG. 14 is a sectional view of the part of the monitor device of FIG. 13, FIGS. 15A-15C show a sequence of steps by which the monitor device may be connected to an exemplary base plate.

FIGS. 13 and 14 are illustrations of a part of the monitor device 6 including a first interface 102. FIG. 14 is a cross sectional view of the monitor device shown in FIG. 13, taken along line 14-14. As shown, the first interface 102 includes a first connector comprising a coupling part 120 and a plurality of terminals, e.g. monitor terminals, such as ground terminal 108, first terminal 110, second terminal 112, third terminal 114, fourth terminal 116 and fifth terminal 118. The first interface 102, e.g., by coupling part 120, is configured to releasably structurally (e.g., mechanically) couple the monitor device 6 to other components of the ostomy system 1, including the first connector 211 of the monitor interface of the base plate and/or sensor assembly part (e.g., FIG. 11) and the first connector 22 of the docking monitor interface (e.g., FIG. 12). The illustrated embodiment of the coupling part 120 comprises a recess 143 defined by a wall portion 142 in the monitor device 6 and one or more tabs 144 extending from the wall portion. The illustrated embodiment includes two tabs 144 extending from the wall portion 142 into the recess 143. To facilitate the mechanical connection of the coupling part 120 with the first connector 211, the recess 143 is sized to fit over the post 500 with the tabs 144 aligned with the upper openings 512 in the slots 504 of the monitor interface of the base plate. Similarly, the recess 143 is sized to fit over the post 500' with the tabs 144 aligned with the upper openings 512' of the docking monitor interface. Coupling part 120 of the monitor device 6 and coupling part 210 of the base plate 4 are configured to cooperate as what are sometimes referred to as bayonet or luer connectors.

The plurality of monitor terminals 108, 110, 112, 114, 116 and 118 are positioned at circumferentially spaced locations within the recess 141 and have associated terminal elements 108A, 110A, 112A, 114A, 116A and 118A. As described in greater detail below, in embodiments the terminal elements 108A, 110A, 112A, 114A, 116A and 118A are located to cause the associated terminals 108, 110, 112, 114, 116 and 118 to electrically connect to the associated terminals 282A, 284A, 286A, 288A, 290A and 292A of the first connector 211 when the monitor device 6 is connected to the base plate 4 and/or the sensor assembly part 700 (i.e., a wired connection). Similarly, in embodiments, the monitor device terminal elements 108A, 110A, 112A, 114A, 116A and 118A are located to cause the associated terminals 108, 110, 112, 114, 116 and 118 to electrically connect to the associated terminals 282A', 284A', 286A', 288A', 290A' and 292A' of the docking station interface first connector 22 when the monitor device 6 is connected to the docking station 20.

For example, a primary terminal, e.g. the ground terminal 108, may be configured to form electrical connection with a primary electrode, such as a ground electrode, e.g. an electrode connected with the ground terminal 282, of the base plate 4 when the monitor device 6 is coupled to the base plate 4, and the primary terminal 108 may be configured to form electrical connection with a primary charge terminal, e.g. the ground terminal 282' of the accessory device 20 when the monitor device 6 is coupled to the accessory device 20.

A secondary terminal, e.g. the first terminal 110, may be configured to form electrical connection with a secondary electrode, such as a first electrode, e.g. an electrode connected with the first terminal 284, of the base plate when the monitor device 6 is coupled to the base plate 4, and the secondary terminal 110 may be configured to form electrical connection with a secondary charge terminal, e.g. the first terminal 284' of the accessory device 20 when the monitor device 6 is coupled to the accessory device 20.

A tertiary terminal, e.g. the second terminal 112, may be configured to form electrical connection with a tertiary electrode, such as a second electrode, e.g. an electrode connected with the second terminal 286, of the base plate when the monitor device 6 is coupled to the base plate 4, and the tertiary terminal 112 may be configured to form electrical connection with a primary data terminal, e.g. the second terminal 286' of the accessory device 20 when the monitor device 6 is coupled to the accessory device 20.

A quaternary terminal, e.g. the third terminal 114, may be configured to form electrical connection with a quaternary electrode, such as a third electrode, e.g. an electrode connected with the third terminal 288, of the base plate when the monitor device 6 is coupled to the base plate 4, and the quaternary terminal 114 may be configured to form electrical connection with a secondary data terminal, e.g. the third terminal 288' of the accessory device 20 when the monitor device 6 is coupled to the accessory device 20.

Figure 15A:
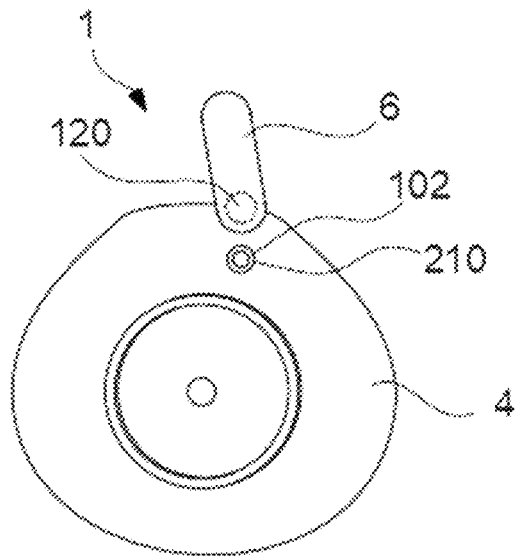
Figure 15B:
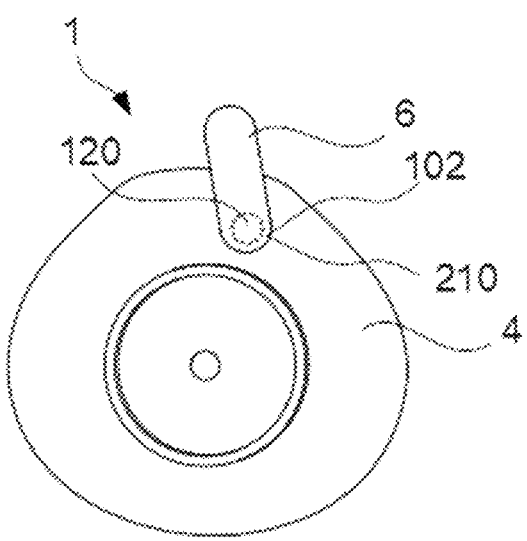
Figure 15C:
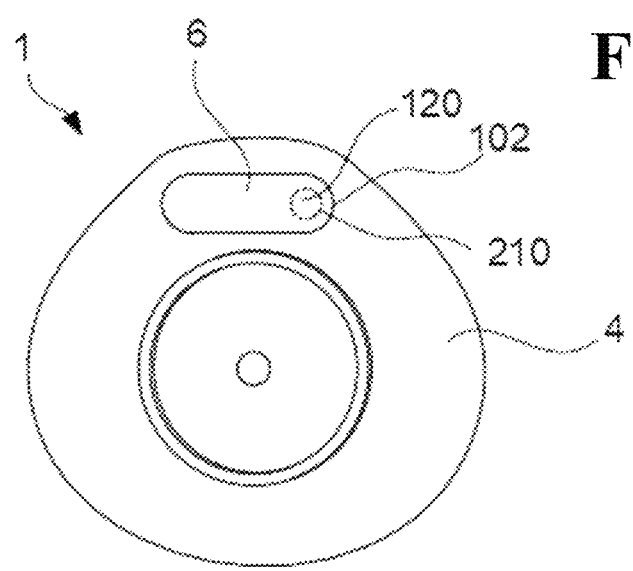

FIGS. 15A-15C illustrate a sequence of steps for the connection of the monitor device 6 to the base plate 4 in accordance with embodiments. The connection of the monitor device 6 to the base plate 4 can also be described with reference to FIG. 11 and FIGS. 13 and 14. As shown in FIGS. 15A and 15B, when attaching the monitor device 6 to the base plate 4, the monitor device 6 is moved to position the coupling part 120 over and in alignment with the coupling part 210 of the base plate 4. To attach the monitor device 6 to the base plate 4, the monitor device is positioned at a first position and orientation or an attachment position and orientation with respect to the base plate (e.g., as shown in FIG. 15B), with the tabs 144 of the monitor coupling part 120 aligned or registered with the openings 512 of the slots 504 of the base plate coupling part 210. At this attachment position the post 500 of the base plate 4 can enter the recess 141 of the monitor device 6. The monitor device 6 is then moved with respect to the base plate 4 to cause the tabs 144 to enter the slots 504 through the openings 512. After the monitor device 6 is positioned on the base plate 4 with the tabs 144 in the slots 504, the monitor device is rotated to a second position and orientation or a connected position and orientation such as that shown in FIG. 15C. During the rotation of the monitor device 6 from the attachment position to the connected position, the tabs 144 are guided in the slots 504, causing the coupling part 120 of the monitor device to mechanically engage and connect to the first connector 211 of the base plate 4. In the illustrated embodiment, the rotation of the monitor device 6 is stopped to register the monitor device at the connected position by the tabs 144 engaging the stops 514 of the base plate coupling part 210. The rotation of the monitor device 6 also causes the terminal elements 108A, 110A, 112A, 114A, 116A and 118A of the monitor device to electrically couple to the terminal elements 282, 284, 286, 288, 290 and 292, respectively of the base plate 4. Other embodiments include other structures on the monitor device 6 and/or base plate 4 to cause the desired registration of the terminal elements 108A, 110A, 112A, 114A, 116A and 118A to terminal elements 282, 284, 286, 288, 290 and 292, respectively, when the monitor device is at the connected position on the base plate.

Features of the monitor device 6 and/or base plate 4 are configured so that each of the desired terminal elements 108A, 110A, 112A, 114A, 116A and 118A of the monitor device will be electrically connected to an appropriate one of the terminal elements 282, 284, 286, 288, 290 and 292, respectively, of the base plate 4 when the monitor device is at the connected position. By way of non-limiting example, the ground terminal element 108A of the first interface 102 of the monitor device will be registered with and electrically connected to the ground terminal element 282 of the base plate first connector 211 when the monitor device is at the connected position.

When the first interface 102 of the monitor device is coupled to the monitor interface of the base plate 4, a first group of the monitor device terminal elements (e.g., one or more of terminal elements 108A, 110A, 112A, 114A, 116A and 118A) are electrically coupled to associated base plate terminal elements (e.g., one or more of terminal elements 282, 284, 286, 288, 290 and 292). The first group of terminal elements, e.g., being coupled to associated monitor device terminal elements, is thereby configured to transmit information from the base plate 4 to the monitor device 6. In embodiments, the first group of terminal elements, e.g., being coupled to associated monitor device terminal elements, is configured to transmit information from the electrode assembly 204 of the base plate 4 to the monitor device 6.

To remove the monitor device 6, the monitor device is rotated from the connected position to the attachment position with respect to the base plate 4. The tabs 144 of the monitor coupling part 120 are thereby moved to the openings 512 in the slots 504 of the base plate first connector 211. The monitor device 6 can then be disengaged and removed from the base plate 4.

Because of the similarity of the structural features of the docking station first connector 22 to those of the base plate first connector 211, the monitor device 6 can be attached to and removed from the docking station 20 in manner similar to that described above by which it is attached to and removed from the base plate 4. When the monitor device 6 is at a connected position on the docking station 20, the terminal elements 108A, 110A, 112A, 114A, 116A and 118A will electrically couple to the terminal elements 282', 284', 286', 288', 290' and 292', respectively, of the docking station first connector 22 (i.e., a wired connection). Features of the monitor device 6 and/or docking station 20 are configured so that each of the desired terminal elements 108A, 110A, 112A, 114A, 116A and 118A of the monitor device will be registered with and electrically connected to an appropriate one of the terminal elements 282', 284', 286', 288', 290' and 292', respectively, of the docking station when the monitor device is at the connected position. By way of non-limiting example, any terminal element(s) of the first interface 102 of the monitor device configured to provide power to the power unit 121 of the monitor device 6 (shown in FIG. 2) will be registered with and/or electrically connected to the terminal element(s) of the docking station first connector 22 that are coupled to the source of power (not shown) in the docking station 20 when the monitor device is at the connected position. In embodiments, the docking station 20 can have more or fewer terminal elements than the monitor device 6 In embodiments, when the monitor device 6 is at the connected position on the base plate 4 (e.g., as shown in FIG. 15C), the processor 101 can generate a monitor-to-base plate signal indicating a monitor-to-base plate state. The monitor-to-baseplate signal can be stored in the memory 106 and/or transmitted by transceiver 124 (e.g., FIG. 2). The processor 101 can also store other data, such as times that the monitor device 6 is in the monitor-to-base plate state. In embodiments, the processor 101 identifies the monitor-to-base plate state by receiving an identification signal from an identification sensor of the monitor device configured to detect an identification element of the base plate. Alternatively or in addition, the monitor-to-base plate signal can be generated based on an evaluation of signals at one or more terminals 108, 110, 112, 114, 116, 118 (FIG. 2), such as respective terminal elements 108A, 110A, 112A, 114A, 116A and 118A. Similarly, in embodiments, when the monitor device 6 is at the connected position on the docking station 20, the processor 101 can generate a monitor-to-docking station signal indicating a monitor-to-docking station state. The monitor-to-docking station signal can be stored in the memory 106 and/or transmitted by transceiver 124. Processor 101 can also store and/or cause the transmission of other data, such as times that the monitor device 6 is in the monitor-to-docking station state. In embodiments, the processor 101 identifies the monitor-to-docking station state by receiving an identification signal from an identification sensor of the monitor device configured to detect an identification element of the docking station. Alternatively or in addition, the monitor-to-docking station signal can be generated based on an evaluation of signals at one or more terminals 108, 110, 112, 114, 116, 118 (FIG. 2), such as respective terminal elements 108A, 110A, 112A, 114A, 116A and 118A.

When the first interface 102 of the monitor device is coupled to the monitor interface of the docking station 20, a second group of the monitor device terminal elements (e.g., one or more of terminal elements 108A, 110A, 112A, 114A, 116A and 118A) are electrically coupled to associated docking station terminal elements (e.g., one or more of terminal elements 282', 284', 286', 288', 290' and 292'). The second group of monitor device terminal elements can be the same as or different than the first group of monitor device terminal elements. In embodiments, the coupled second group of terminal elements is thereby configured to transmit electrical charge from the docking station 20 to the monitor device 6. In embodiments, the second group of terminal elements, e.g., being coupled to associated docking station terminal elements is thereby configured to transmit information from the monitor device 6 to the docking station 20 (e.g., information stored in the memory 106). In embodiments, the second group of terminal elements, e.g., being coupled to associated docking station terminal elements is thereby configured to transmit information from the docking station 20 to the monitor device 6 (e.g., configuration information to be stored in memory 106).

One or more of the terminals 108, 110, 112, 114, 116, 118, such as one or more of the terminal elements 108A, 110A, 112A, 114A, 116A, 118A of the first interface 102 of monitor device 6 can provide different functionality (i.e., be used for different purposes), when the monitor device is connected to an accessory device such as a docking station and when the monitor device is connected to a base plate. For example, when the monitor device 6 is connected to the base plate 4 (FIG. 11), terminal element 108A can function to couple one of the electrodes 224, 226, 228, 230 or 232 of the base plate 4 to the processor of the monitor device 6. When the monitor device 6 is connected to the docking station 20 (FIG. 12), the terminal element 108A can function to couple a power unit of the docking station to the power unit of the monitor device 6.

Control or other devices such as switches or multiplexers of the monitor device 6, which can for example be provided as components of the first interface 102, can cause the terminal elements 108A, 110A, 112A, 114A, 116A and 118A of the first interface 102 to be coupled to the desired respective components on the base plate 4 and accessory device such as docking station 20.

Figure 16:
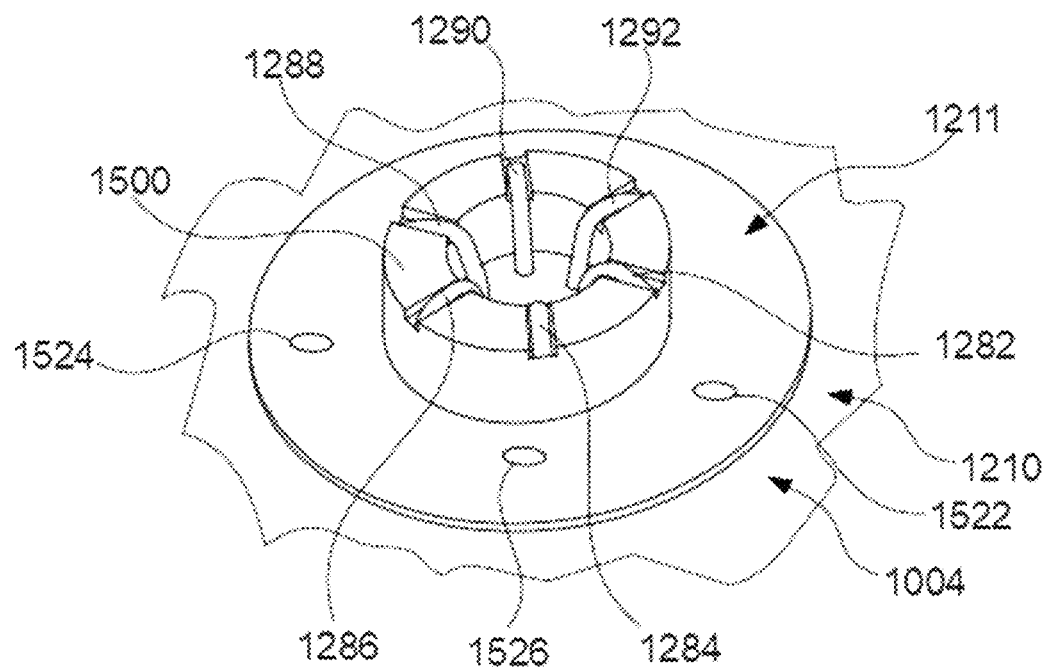
FIG. 16 is an isometric illustration of an exemplary monitor interface.

FIG. 16 is a diagrammatic isometric view of a part of a base plate/sensor assembly part 1004 including a first connector 1211 of a monitor interface of the base plate/sensor assembly part 1004 in accordance with embodiments. As shown, the first connector 1211 comprises a coupling part 1210 configured to releasably couple the base plate/sensor assembly part 1004 to a monitor device, and thus forming a releasable coupling. The first connector 1211 comprises a plurality of terminals 1282, 1284, 1286, 1288, 1290 and 1292. The coupling part 1210 comprises a group of one or more magnetic elements 1522, 1524 and 1526. As shown, the magnetic elements 1522, 1524 and 1526 are located at spaced-apart locations on the base plate/sensor assembly part 1004, e.g., around the post 1500. Other embodiments of coupling part 1210 have more or fewer magnetic elements, and/or the magnetic elements may be positioned at different locations on the base plate/sensor assembly part 1004. Magnetic elements 1522, 1524 and 1526 are magnets and/or ferromagnetic materials (e.g., iron) in embodiments. Magnetic elements 1522, 1524 and 1526 can be on the base plate/sensor assembly part 1004. Magnetic elements 1522, 1524 and 1526 can have their poles at any desired orientations (e.g., at radial and/or axial orientations). Other than the magnetic elements 1522, 1524 and 1526, the base plate/sensor assembly part 1004 and/or the coupling part 1210 can be substantially the same as or similar to the base plate 4 and/or sensor assembly part 700 and/or the coupling part 210 described above (e.g., in connection with FIG. 11), and similar features are identified by similar reference numbers. By way of example, embodiments of base plates and/or sensor assembly parts can include features of coupling parts 210 and/or 1210.

Figure 17:
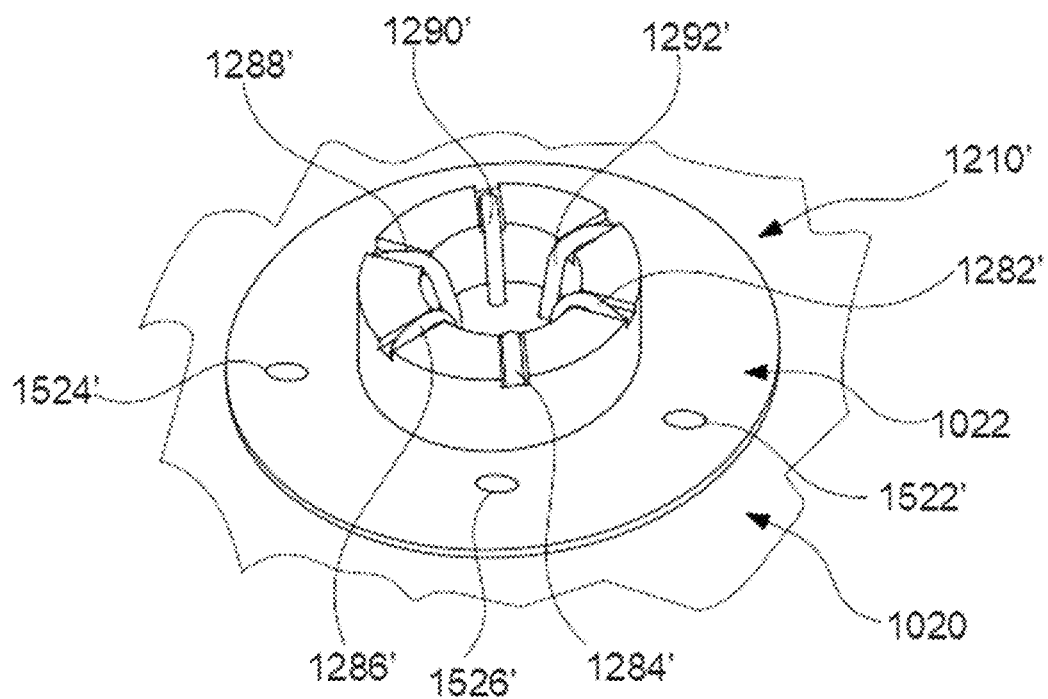
FIG. 17 is an isometric illustration of an exemplary docking monitor interface.

FIG. 17 is a diagrammatic isometric view of a part of docking station 1020 including a first connector 1022 of a docking monitor interface of the docking station 1020. As shown, the first connector 1022 comprises a coupling part 1210' configured to releasably couple the docking station 1020 to a monitor device, and thus forming a releasable coupling. The first connector 1022 comprises a plurality of terminals 1282', 1284', 1286', 1288', 1290' and 1292'. The coupling part 1210' comprises a group of one or more magnetic elements 1522', 1524' and 1526'. As shown, the magnetic elements 1522', 1524' and 1526' are located at spaced-apart locations on the docking station 1020. Other embodiments of coupling part 1210' have more or fewer magnetic elements, and/or the elements may be positioned at different locations on the docking station 1020. Magnetic elements 1522', 1524' and 1526' are magnets and/or ferromagnetic materials (e.g., iron) in embodiments. Magnetic elements 1522', 1524' and 1526' can be on the docking station 1020. Magnetic elements 1522', 1524' and 1526' may have their poles at any desired orientations (e.g., at radial and/or axial orientations). Other than the magnetic elements 1522', 1524' and 1526', the docking station 1020 and/or coupling part 1210' can be substantially the same as or similar to the docking station 20 and/or the coupling part 210' described above (e.g., in connection with FIG. 12), and similar features are identified by similar reference numbers. By way of example, embodiments of docking stations can include features of coupling parts 210' and/or 1210'.

Figure 18:
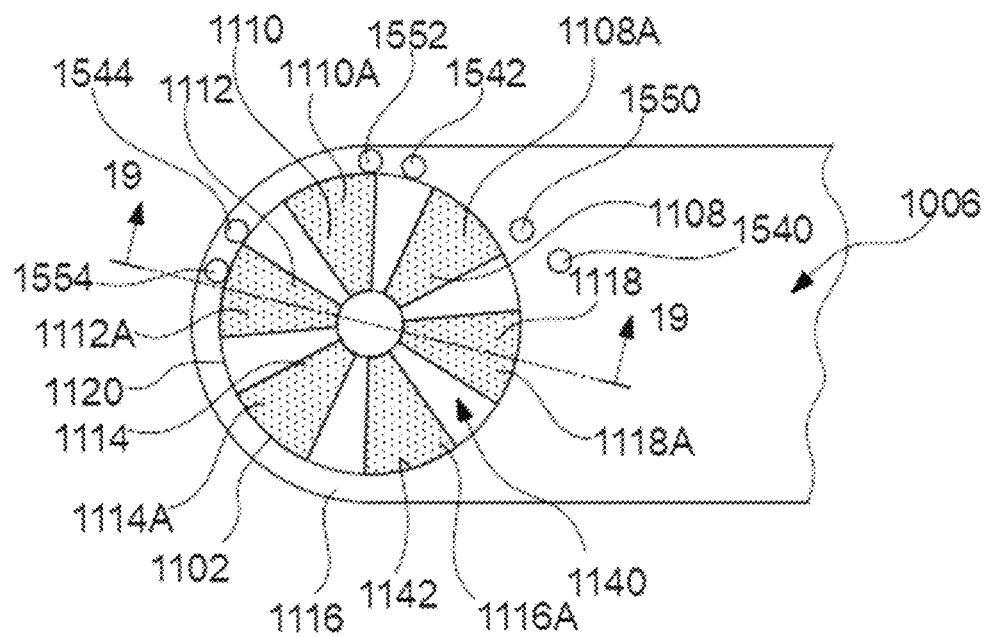
FIG. 18 is an illustration of a part of an exemplary monitor device.
Figure 19:
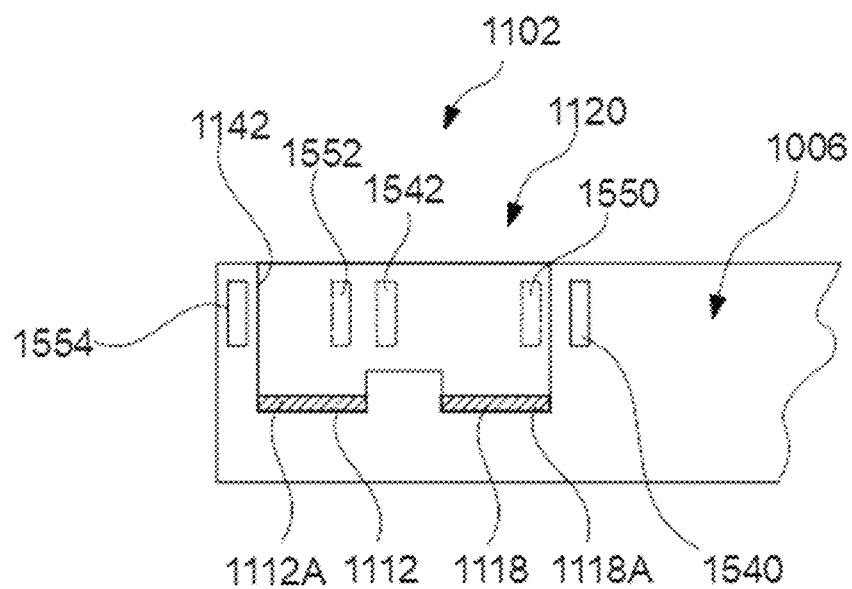
FIG. 19 is a sectional view of the part of the monitor device of FIG. 18.

FIGS. 18 and 19 are diagrammatic illustrations of a part of a monitor device 1006 including a first interface 1102. FIG. 19 is a cross sectional view of the monitor device as indicated by the line 19-19 in FIG. 18. As shown, the first interface 1102 includes a first connector comprising a coupling part 1120 and a plurality of terminals such as ground terminal 1108, first terminal 1110, second terminal 1112, third terminal 1114, fourth terminal 1116 and fifth terminal 1118. The first interface 1102 (e.g., by coupling part 1120), is configured to releasably and mechanically (e.g., structurally) couple the monitor device 1006 to other components of an ostomy system, including the first connector 1211 of the monitor interface of the base plate (e.g., FIG. 16) and the first connector 1022 of the docking monitor interface of the docking station (e.g., FIG. 17). The coupling part 1120 comprises a first group of one or more magnetic elements 1540, 1542 and 1544 and a second group of magnetic elements 1550, 1552 and 1554. The magnetic elements 1540, 1542, 1544, 1550, 1552 and 1554 are magnets and/or ferromagnetic materials (e.g., iron) in embodiments. Other than the magnetic elements 1540, 1542, 1544, 1550, 1552 and 1554, the monitor device 1006 can be substantially the same as or similar to the monitor device 6 described above (e.g., in connection with FIGS. 13 and 14), and similar features are identified by similar reference numbers. By way of example, embodiments of monitor devices can include features of coupling parts 1120 and 120.

The first group of magnetic elements 1540, 1542 and 1544, are configured to couple to the group of magnetic elements on the base plate 1004. By way of example, the magnetic element 1540, 1542 and 1544 can be located on the monitor device 1006 at locations that will cause those magnetic elements to be attracted to the magnetic elements 1522, 1526 and 1524 of the base plate coupling part 1210 of base plate 1004 shown in FIG. 16. In addition to providing the releasable coupling function, the magnetic elements 1540, 1542 and 1544 of the monitor device 1006 and the magnetic elements 1522, 1526 and 1524 of the base plate 1004 are configured (e.g., located) to cause the registration and/or interconnection of the desired terminals 1108, 1110, 1112, 1114 1116 and 1118 of the monitor device to the desired terminals 1282, 1284, 1286, 1288, 1290 and 1292 of the base plate 1004. In embodiments, one or more of the magnetic elements 1540, 1542 and 1544 of the monitor device 1006 has a first pole (e.g., a north-seeking pole) that faces the base plate 1004 (i.e., the magnetic elements are arranged to provide a first magnetic field orientation), and the corresponding magnetic elements 1522, 1526 and 1524 of the base plate 1004 has a second pole (e.g., a south-seeking pole) to cause the magnetic attraction of the associated magnetic elements. In embodiments, one or one or more of the magnetic elements 1540, 1542 and 1544 of the monitor device 1006 and/or one or more of the magnetic elements such as 1522, 1526 and 1524 of the base plate 1004 is ferro-magnetic material, and the corresponding magnetic elements on the monitor device and/or base plate is a magnetic element to cause the magnetic attraction of the associated magnetic elements.

In embodiments, the second group of magnetic elements 1550, 1552 and 1554 are configured to prevent the second group of magnetic elements from being magnetically attracted to the magnetic elements 1522, 1526 and 1524 of the base plate 1004. By way of example, the second group of magnetic elements 1550, 1552 and 1554 on the monitor device 1006 can be located at locations that prevent the second group of magnetic elements 1550, 1552, 1554 from being attracted to the magnets on the base plate 1004, and/or the poles of the second group of magnetic elements on the monitor device can be the same as the poles of the magnetic elements on the base plate so as to repel one another.

The second group of magnetic elements 1550, 1552 and 1554, may be configured to couple to the group of magnetic elements on the docking station 1020. By way of example, the magnetic elements 1550, 1552 and 1554 can be located on the monitor device 1006 at locations that will cause those magnetic elements to be attracted to the magnetic elements 1522', 1526' and 1524' of the docking station coupling part 1210' of the docking station 1020 shown in FIG. 17. In addition to providing the releasable coupling function, the magnetic elements 1550, 1552 and 1554 of the monitor device 1006 and the magnetic elements 1522', 1526' and 1524' of the docking station 1020 may be configured (e.g., located) to cause the registration and interconnection of the desired terminals 1108, 1110, 1112, 1114 1116 and 1118 of the monitor device to the desired terminals 1282', 1284', 1286', 1288', 1290' and 1292' of the docking station. In embodiments, one or more of the magnetic elements such as 1550, 1552 and 1554 of the monitor device 1006 has a first pole (e.g., a north-seeking pole) that faces the docking station 1020, and the corresponding magnetic elements 1522', 1526' and 1524' of the docking station has a second pole (e.g., a south pole) to cause the magnetic attraction of the associated magnetic elements. In embodiments, one or one or more of the magnetic elements 1550, 1552 and 1554 of the monitor device 1006 and/or one or more of the magnetic elements 1522', 1526' and 1524' of the docking station 1020 is ferro-magnetic material, and the corresponding magnetic elements on the monitor device and/or docking station is a magnetic element to cause the magnetic attraction of the associated magnetic elements. In embodiments one or more of the magnetic elements 1550, 1552 and 1544 of the monitor device 1006 has a second pole (e.g., a south-seeking pole) that faces the base plate 1004 (i.e., the magnetic elements are arranged to provide a second magnetic field orientation).

In embodiments, the first group of magnetic elements 1540, 1542 and 1544 are configured to prevent the first group of magnetic elements from being magnetically attracted to the magnetic elements 1522', 1526' and 1524' of the docking station 1020. By way of example, the first group of magnetic elements 1540, 1542 and 1544 on the monitor device 1006 can be located at locations that prevent them from being attracted to the magnets on the docking station 1020, and/or the poles of the first group of magnetic elements on the monitor device can be the same as the poles of the magnetic elements on the docking station so as to repel one another.

In embodiments, the terminals of the monitor device 6 are configured to electrically couple to other components of the ostomy system such as to the terminals of the base plate and/or docking station through a wireless connection. For example, terminals 108, 110, 112, 114 116 and 118 of the monitor device 6 and terminals 282, 284, 286, 288, 290 and 292 of the base plate 4 can be Bluetooth or other radio frequency transceivers.

Figure 20:
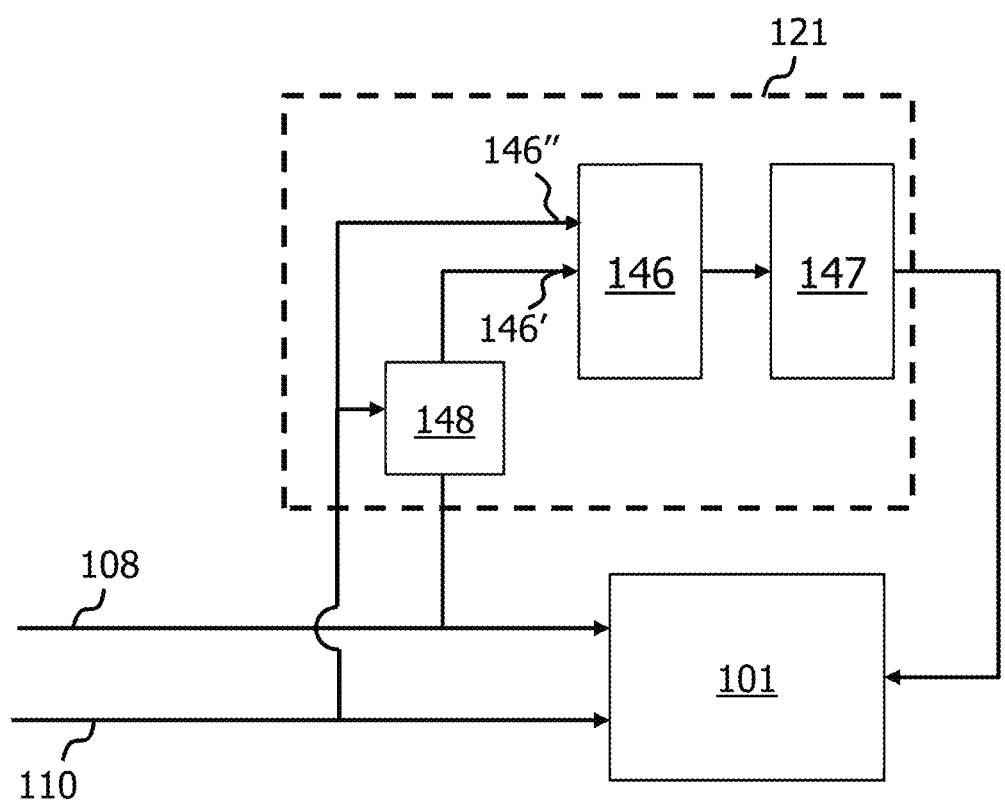
FIG. 20 is a schematic block diagram of part of an exemplary monitor device.

FIG. 20 is a schematic block diagram of part of an exemplary monitor device 6. The monitor device 6 may, e.g. in addition to the illustrated features, comprise one or more of the features as described previously, e.g. in relation to FIG. 2. In the illustrated example, a primary terminal, such as a ground terminal 108, and a secondary terminal, such as first terminal 110 is illustrated. The monitor device furthermore comprises a processor 101 and a power unit 121. The power unit powers the processor 101. The primary terminal 108 and the secondary terminal 110 are connected to the processor 101 and the power unit 121.

The processor may retrieve ostomy data from the primary terminal 108 and the secondary terminal 110, e.g. by retrieving a resistance between the two terminals 108, 110, when the primary terminal 108 and the secondary terminal 110 are coupled to terminals of a base plate.

The power unit 121 comprises a battery 147 and charging circuit 146. The charging circuit 146 is configured to charge the battery 147 by a voltage difference between a primary charging terminal 146' and a secondary charging terminal 146". Furthermore, the power unit 121 comprises a charging switch 148 operable based on a voltage difference between the primary terminal 108 and the secondary terminal 110. The charging-switch 148 is configured to electrically connect the primary terminal 108 to the primary charging terminal 146' when the voltage difference between the primary terminal 108 and the secondary terminal 110 is above a voltage threshold. The secondary terminal 110 is electrically connected to the secondary charging terminal 146" of the charging circuit 146. In embodiments, the charging-switch 148 or a second charging-switch may be configured to electrically connect the secondary terminal 110 to the secondary charging terminal 146" when the voltage difference between the primary terminal 108 and the secondary terminal 110 is above a voltage threshold.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

Exemplary embodiments of the present disclosure are set out in the following items:

1. A monitor device for an ostomy system, the monitor device comprising:
   a housing;
   a power unit disposed in the housing;
   a processor disposed in the housing; and
   a first interface including (i) a plurality of monitor terminals configured to electrically couple the monitor device to a base plate for the ostomy system and a docking station for the ostomy system, and (ii) a coupling part configured to releasably and structurally couple the monitor device to the base plate and the docking station.
2. The monitor device of item 1, wherein the first interface of the monitor device is configured to (i) couple the monitor device to the base plate to establish a monitor-to-base plate state and (ii) couple the docking station to establish a monitor-to-docking station state.
3. The monitor device of any of the preceding items, wherein the processor is configured to (i) generate a monitor-to-base plate signal when the monitor device is coupled with the base plate, and (ii) generate a monitor-to-docking station signal when the monitor device is coupled with the docking station.
4. The monitor device of any of the preceding items, wherein the coupling part of the monitor device is configured to be releasably and structurally coupled to a base plate coupling part of the base plate.
5. The monitor device of any of the preceding items, wherein the coupling part of the monitor device is configured to be releasably and structurally coupled to a docking station coupling part of the docking station.
6. The monitor device of any of the preceding items, wherein the plurality of monitor terminals of the monitor device comprises a plurality of terminal elements, the plurality of terminal elements including a first group of terminal elements configured to electrically couple with the base plate.
7. The monitor device of items 6, wherein at least one of the first group of terminal elements is configured to transmit information from the base plate to the monitor device.
8. The monitor device of any of the preceding items, wherein the plurality of terminal elements comprises a second group of terminal elements configured to electrically couple with the docking station.
9. The monitor device of item 8, wherein at least one of the second group of terminal elements is configured to transmit electrical charge from the docking station to the monitor device.
10. The monitor device of any of items 8-9, wherein at least one of the second group of terminal elements is configured to transmit information from the monitor device to the docking station and/or transmit information from the docking station to the monitor device.
11. The monitor device of any of the preceding items, wherein the coupling part of the monitor device comprises a first group of monitor magnetic members configured to be magnetically coupled to a group of base plate magnetic members of the base plate.
12. The monitor device of any of the preceding items, wherein the coupling part of the monitor device comprises a second group of monitor magnetic members configured to be magnetically coupled to a group of docking station magnetic members of the docking station.
13. The monitor device of item 12 as dependent on item 11, wherein the first group of monitor magnetic members are configured to magnetically repel the group of docking station magnetic members.

14. The monitor device of item 12 as dependent on item 11, wherein the second group of monitor magnetic members are configured to magnetically repel the group of base plate magnetic members.
15. The monitor device of any of items 12-14 as dependent on item 11, wherein one or more magnetic members of the first group of monitor magnetic members are arranged to provide a first magnetic field orientation, and one or more magnetic members of the second group of monitor magnetic members are arranged to provide a second magnetic field orientation that is opposite the first magnetic field orientation.
16. The monitor device of any of the preceding items, wherein the power unit comprises an energy storage member including at least one of a primary battery, a secondary battery, or a supercapacitor.
17. The monitor device of any of the preceding items, wherein the plurality of monitor terminals is configured to electrically couple the monitor device to the base plate and the docking station through a wired connection.
18. The monitor device of any of the preceding items, wherein the plurality of monitor terminals is configured to electrically couple the monitor device to the base plate and the docking station through a wireless connection.

LIST OF REFERENCES 1 ostomy system
2 ostomy appliance
4 base plate
6 monitor device
8 accessory device
10 server device
12 network
14 coupling member
16 coupling ring
18 stoma-receiving opening
20 docking station
22 first connector of docking station
24 user interface
100 monitor device housing
101 processor
102 first interface
104 second interface
106 memory
108 ground terminal of monitor device
108A terminal element
110 first terminal of monitor device
110A terminal element
112 second terminal of monitor device
112A terminal element
114 third terminal of monitor device
114A terminal element
116 fourth terminal of monitor device
116A terminal element
118 fifth terminal of monitor device
118A terminal element
120 coupling part
121 power unit
122 antenna
124 wireless transceiver
126 loudspeaker
128 haptic feedback element
140 sensor unit
143 recess
142 wall portion
144 tabs
146 charging circuit
147 battery
148 charging switch
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
210' coupling part
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
217 connection part(s)
218 masking element
218A distal surface of masking element
218B proximal surface of masking element
220 electrode configuration
222 ground electrode
222A ground connection part
222B ground sensing part
224 first electrode
224A first connection part
226 second electrode
226A second connection part
228 third electrode
228A third connection part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening 256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282' terminal element
282A ground terminal
282A' ground terminal
284 first terminal element
284' terminal element
284A first terminal
284A' terminal
286 second terminal element
286' terminal element
286A second terminal
286A' terminal
288 third terminal element
288' terminal element
288A third terminal
288A' terminal
290 fourth terminal element
290' terminal element
290A fourth terminal
290A' terminal
292 fifth terminal element
292' terminal element
292A fifth terminal
292A' terminal
500 post
500' post
502 threads
504 slots
506 projections
508 upper surface
510 lower surface
512 upper opening
512' upper openings
514 stops
700 sensor assembly part
1004 base plate
1006 monitor device
1020 docking station
1022 first connector
1102 first interface
1108 ground terminal
1110 first terminal
1112 second terminal
1114 third terminal
1116 fourth terminal
1118 fifth terminal
1120 coupling part
1210 coupling part
1210' coupling part
1211 first connector
1282 terminal
1282' terminal
1284 terminal
1284' terminal
1286 terminal
1286' terminal
1288 terminal
1288' terminal
1290 terminal
1290' terminal
1292 terminal
1292' terminal
1500 post
1522 magnetic element
1522' magnetic element
1524 magnetic element
1524' magnetic element
1526 magnetic element
1526' magnetic element
1540 magnetic element
1542 magnetic element
1544 magnetic element
1552 magnetic element
1554 magnetic element

The invention claimed is:

1. A method of monitoring performance of an ostomy device, the method comprising:
providing an ostomy appliance comprising a sensor and a base plate, where the base plate is attachable to skin of a user by an adhesive disposed on a proximal side of the base plate and the sensor is distal of the adhesive;
providing a monitor device electrically attachable to the sensor of the ostomy appliance;
monitoring, with the sensor, moisture information sensed between the skin of the user and the adhesive on the proximal side of the ostomy appliance;
collecting the moisture information with the monitor device; and
transferring, with the monitor device, the moisture information to an accessory device.

2. The method of claim 1, further comprising:
determining moisture propagation in the adhesive; and
transferring, with the monitor device, the moisture propagation information to the accessory device.

3. The method of claim 1, further comprising:
determining a rapidness of moisture propagation in the adhesive; and
transferring, with the monitor device, the moisture propagation information to a mobile phone.

4. The method of claim 1, further comprising:
determining moisture propagation in the adhesive;
providing, with the monitor device, the moisture propagation information to the user; and
providing, with the accessory device, an indication to the user of a remaining time frame for replacing the ostomy appliance.

5. The method of claim 4, further comprising informing the user, with the accessory device, to replace the ostomy appliance with a new ostomy appliance prior to the user experiencing leakage of stoma output between the skin of the user and the ostomy appliance.

6. The method of claim 4, further comprising informing the user, with the accessory device, to replace the ostomy appliance with a new ostomy appliance prior to the user experiencing damage to the skin of the user.

7. The method of claim 1, wherein the monitor device further comprises a first interface comprising a monitor coupling part, the method further comprising:

coupling the monitor device electrically and mechanically to the sensor of the ostomy appliance with the monitor coupling part.

8. The method of claim 1, wherein the accessory device comprises a docking station, the method further comprising:
uncoupling the monitor device from the sensor of the ostomy appliance;
coupling the monitor device electrically and mechanically to the docking station; and
transferring the moisture information from the monitor device to the docking station.

9. The method of claim 1, wherein the monitor device further comprises a first interface comprising a monitor coupling part and the accessory device comprises a docking station comprising a docking monitor interface, the method further comprising:
coupling the monitor coupling part of the monitor device electrically and mechanically to the sensor of the ostomy appliance;
collecting moisture propagation information relative to the adhesive with the monitor device;
decoupling the monitor device electrically and mechanically from the ostomy appliance;
coupling the monitor device electrically and mechanically to the docking monitor interface of the docking station; and
transferring the moisture propagation information from the monitor device to the docking station and transferring the moisture propagation information from the docking station to the user.

10. The method of claim 1, wherein the accessory device comprises a mobile phone, the method further comprising:
wirelessly transferring the moisture information from the monitor device to the mobile phone.

11. The method of claim 1, wherein the monitor device further comprises a power unit and a first interface comprising a plurality of terminals, the power unit comprising a battery and a charging circuitry connected to the battery and to the plurality of terminals of the first interface, the method further comprising:
coupling the plurality of terminals of the first interface of the monitor device electrically to the accessory device; and
charging the battery of the monitor device, with the charging circuitry, when the plurality of terminals of the first interface is coupled to the accessory device.

12. The method of claim 1, wherein the sensor comprises a plurality of electrode pairs, the method further comprising:
determining moisture propagation in the adhesive by sensing resistance between a first electrode pair and a second electrode pair of the plurality of electrode pairs; and
transferring, with the monitor device, the moisture propagation information to the accessory device.

13. The method of claim 1, wherein the sensor comprises a plurality of electrode pairs, the method further comprising:
determining moisture propagation in the adhesive by sensing a rate of change in resistance between a first electrode pair and a second electrode pair of the plurality of electrode pairs; and
transferring, with the monitor device, the moisture propagation information to the accessory device.

14. The method of claim 1, further comprising:
detecting, with the sensor, stoma leakage information sensed between the skin of the user and the adhesive on the proximal side of the ostomy appliance; and
collecting the stoma leakage information with the monitor device; and
communicating the stoma leakage information to the user via the monitor device.

15. The method of claim 14, further comprising communicating the stoma leakage information from the monitor device to the user via the accessory device.

* * * * *